(12) United States Patent
Kilgard et al.

(10) Patent No.: US 12,151,104 B2
(45) Date of Patent: *Nov. 26, 2024

(54) METHODS, SYSTEMS, AND DEVICES FOR PAIRING VAGUS NERVE STIMULATION WITH MOTOR THERAPY IN STROKE PATIENTS

(71) Applicant: Board of Regents, The University of Texas System, Austin, TX (US)

(72) Inventors: Michael P. Kilgard, Richardson, TX (US); Navzer Engineer, Plano, TX (US); David Michael Pierce, Plano, TX (US); Robert L. Rennaker, Sachse, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/310,935

(22) Filed: May 2, 2023

(65) Prior Publication Data
US 2023/0264023 A1 Aug. 24, 2023

Related U.S. Application Data

(63) Continuation of application No. 15/382,970, filed on Dec. 19, 2016, now Pat. No. 11,638,824, which is a
(Continued)

(51) Int. Cl.
*A61N 1/36* (2006.01)
*A61B 5/11* (2006.01)
(Continued)

(52) U.S. Cl.
CPC ..... *A61N 1/36067* (2013.01); *A61N 1/36003* (2013.01); *A61N 1/36053* (2013.01);
(Continued)

(58) Field of Classification Search
CPC ............ A61N 1/36067; A61N 1/36003; A61N 1/36053; A61N 1/36092; A61N 1/361;
(Continued)

(56) References Cited

U.S. PATENT DOCUMENTS

| 5,299,569 A | 4/1994 | Wernicke et al. |
| 6,221,908 B1 | 4/2001 | Kilgard et al. |

(Continued)

OTHER PUBLICATIONS

German Office Action issued in corresponding German Patent Application No. 11 2009 005 564.8, dated Oct. 24, 2023, pp. 1-9.
(Continued)

*Primary Examiner* — Mallika D Fairchild
(74) *Attorney, Agent, or Firm* — Hauptman Ham, LLP

(57) ABSTRACT

A motor-deficit-therapeutic method (for treatment of a patient who has hemiparesis) includes: providing, to the patient afflicted with a hemiparesis, a neurostimulator configured to stimulate a vagus nerve of the patient using electrical, magnetic, optical, acoustic or mechanical stimulation; and initiating stimulation of the vagus nerve by the neurostimulator so that at least a portion of the stimulation occurs at least during performance by the patient of a motor therapy session which is hemiparesis-therapeutic, thereby improving the patient's hemiparesis.

68 Claims, 13 Drawing Sheets

Related U.S. Application Data continuation of application No. 14/252,727, filed on Apr. 14, 2014, now Pat. No. 9,522,272, which is a continuation of application No. 13/651,349, filed on Oct. 12, 2012, now Pat. No. 8,700,145, application No. 18/310,935 is a continuation-in-part of application No. 13/095,570, filed on Apr. 27, 2011, now Pat. No. 9,089,703, which is a continuation-in-part of application No. 12/485,040, filed on Jun. 15, 2009, now Pat. No. 9,089,707.

(60) Provisional application No. 61/699,470, filed on Sep. 11, 2012, provisional application No. 61/614,369, filed on Mar. 22, 2012, provisional application No. 61/598,185, filed on Feb. 13, 2012, provisional application No. 61/558,287, filed on Nov. 10, 2011, provisional application No. 61/627,532, filed on Oct. 13, 2011, provisional application No. 61/328,621, filed on Apr. 27, 2010, provisional application No. 61/077,648, filed on Jul. 2, 2008, provisional application No. 61/078,954, filed on Jul. 8, 2008, provisional application No. 61/086,116, filed on Aug. 4, 2008, provisional application No. 61/149,387, filed on Feb. 3, 2009.

(51) Int. Cl.
*A61N 1/372* (2006.01)
*A61N 2/00* (2006.01)
*A61N 7/00* (2006.01)
*G09B 23/28* (2006.01)

(52) U.S. Cl.
CPC ......... *A61N 1/36092* (2013.01); *A61N 1/361* (2013.01); *A61N 1/36103* (2013.01); *A61N 1/36139* (2013.01); *A61N 1/36178* (2013.01); *A61N 1/37217* (2013.01); *A61N 1/37235* (2013.01); *A61N 1/37247* (2013.01); *A61N 2/006* (2013.01); *A61N 7/00* (2013.01); *G09B 23/28* (2013.01); *A61B 5/1124* (2013.01); *A61N 1/36132* (2013.01); *A61N 2007/0026* (2013.01)

(58) Field of Classification Search
CPC ............ A61N 1/36103; A61N 1/36139; A61N 1/36178; A61N 1/37217; A61N 1/37235; A61N 1/37247; A61N 1/36132; A61N 1/36034; A61N 1/36171
See application file for complete search history.

(56) References Cited

U.S. PATENT DOCUMENTS

| | | | |
|---|---|---|---|
| 6,556,868 | B2 | 4/2003 | Naritoku et al. |
| 6,622,038 | B2 | 9/2003 | Barrett et al. |
| 2002/0146672 | A1 | 10/2002 | Burdea et al. |
| 2003/0093012 | A1 | 5/2003 | Smyser et al. |
| 2006/0055706 | A1 | 3/2006 | Perlman et al. |
| 2006/0178703 | A1 | 8/2006 | Huston et al. |
| 2007/0100392 | A1 | 5/2007 | Maschino et al. |
| 2007/0179534 | A1 | 8/2007 | Firlik et al. |
| 2007/0179558 | A1 | 8/2007 | Gliner et al. |
| 2008/0103548 | A1 | 5/2008 | Fowler et al. |
| 2008/0208266 | A1 | 8/2008 | Lesser et al. |
| 2008/0243196 | A1 | 10/2008 | Libbus et al. |
| 2009/0221928 | A1 | 9/2009 | Einav et al. |
| 2010/0016766 | A1 | 1/2010 | Zhang et al. |
| 2010/0105991 | A1 | 4/2010 | Te Vrugt et al. |

OTHER PUBLICATIONS

Naritomi H, Krieger DW (eds): Clinical Recovery from CNS Damage.Front Neurol Neurosci. Basel, Karger, 2013, vol. 32, pp. 1-8 (DOI: 10.1159/000346405).

McKay, Erin, and Scott E. Counts. "Multi-Infarct Dementia: A Historical Perspective," Dementia and Geriatric Cognitive Disorders Extra, Karger Publishers, May 4, 2017, https://www.karger.com/Article/Fulltext/470836; DOI https://doi.org/10.1159/000470836.

Apraxia, strokeengine.com, Aug. 28, 2020, URL=https://strokengine.ca/en/consequences/apraxia/).

"Sleep-Dependent Learning and Memory Consolidation," Walker et al., Neuron, vol. 44, pp. 121-133, Sep. 30, 2004, URL= https://www.sciencedirect.com/science/article/pii/S0896627304005409; DOI= https://doi.org/10.1016/j.neuron.2004.08.031.

"Neurology: a Queen Square textbook," edited by Charles Clarke et al., Wiley-Blackwell, edited by Charles Clarke et al., 2008, ISBN 978-1-4051-3443-9, pp. v and 109-187.

"Clinical Overview and Phenomenology of Movement Disorders," Chapter 1 of Principles and Practice of Movement Disorders (Second Edition), Fahn, Stanle, et al. Saunders, an imprint of Elsevier Inc., 2011, First Edition 2007, pp. 1-2, 10.1016/B978-1-4377-2369-4.00001-9.

"Parkinson's disease misdiagnosed as stroke," Caslake, Robert, et al. Case Reports 2009; 2009:bcr0720080558, URL=https://casereports.bmj.com/content/2009/bcr.07.2008.0558.

METHODS, SYSTEMS, AND DEVICES FOR PAIRING VAGUS NERVE STIMULATION WITH MOTOR THERAPY IN STROKE PATIENTS

CROSS-REFERENCE TO RELATED APPLICATIONS

This application claims priority to U.S. patent application Ser. No. 15/382,970, filed Dec. 16, 2016, which is a Continuation Application of U.S. patent application Ser. No. 14/252,727, filed Apr. 14, 2014, now U.S. Pat. No. 9,522,272, issued Dec. 20, 2016, which is a Continuation Application of U.S. application Ser. No. 13/651,349, filed Oct. 12, 2012, now U.S. Pat. No. 8,700,145, issued Apr. 15, 2014, which claims priority to the benefit of U.S. Provisional Patent Application No. 61/699,470, filed Sep. 11, 2012, U.S. Provisional Patent Application No. 61/614,369, filed Mar. 22, 2012, U.S. Provisional Patent Application No. 61/598,185, filed Feb. 13, 2012, U.S. Provisional Patent Application No. 61/558,287, filed Nov. 10, 2011, and U.S. Provisional Patent Application No. 61/627,532, filed Oct. 13, 2011. This application is also a Continuation-In-Part of U.S. patent application Ser. No. 13/095,570, filed Apr. 27, 2011, which claims the benefit of U.S. Provisional Patent Application No. 61/328,621, filed Apr. 27, 2010 and which is a Continuation-In-Part of U.S. patent application Ser. No. 12/485,040, filed Jun. 15, 2009, which claims the benefit of: U.S. Provisional Patent Application No. 61/077,648, filed Jul. 2, 2008; U.S. Provisional Patent Application No. 61/078,954, filed Jul. 8, 2008; U.S. Provisional Patent Application No. 61/086,116, filed Aug. 4, 2008; and U.S. Provisional Patent Application No. 61/149,387, filed Feb. 3, 2009. All of these applications are incorporated herein by reference as if reproduced in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Stroke is a leading cause of adult disability in the United States, with upper motor deficits being the primary result of the disability. These motor disabilities greatly affect quality of life for the patient and their loved ones. In addition, the loss of motor function exacts a financial toll on the healthcare system of nearly $70 billion yearly. Patients with hemiplegia or hemiparesis generally regain walking without the use of an assistive device while only half to one-third of patients regain some degree of use of their upper extremity, even after intensive rehabilitation therapy. The severe functional impairment affects occupational performance, and as a result, few stroke victims are able to return to work. Upper limb motor disabilities from stroke have an unfavorable effect on the activities of daily living critically affecting the quality of life for the stroke victim as well as family members and caregivers.

Physical rehabilitation can result in significant improvements in motor outcomes after stroke. Improvements in recovery of upper extremity function have also been reported for electromyographic feedback, motor imagery, robotics, and repetitive task practice, though large scale clinical trials have yet to be implemented. Unfortunately for most patients, the gains are not enough to have a large impact on daily living. Further, current rehabilitative therapies, such as constraint-induced movement therapy, are restricted to individuals with mild to moderate deficits. Few options are available for those stroke survivors with moderate to severe deficits. Therefore, there is still a tremendous need for methods that improve recovery of function even further.

To enhance recovery further, adjuvant therapies have been tried. For example, amphetamines can be effective at enhancing recovery of motor abilities beyond that seen with physical rehabilitation alone; however, even the positive results for motor outcomes are only incremental, and amphetamine use has many well-known side effects. Several small, randomized controlled trials have shown that epidural stimulation significantly improves motor recovery in animal models and in human stroke survivors. Unfortunately, the method requires brain surgery associated with the potential for significant complications and is not likely to reach widespread clinical use in stroke patients. Also, a recent randomized clinical trial failed to demonstrate improved efficacy compared with intensive physical rehabilitation.

Less invasive methods for cortical stimulation have also been combined with physical rehabilitation. Again, however, while real gains in function are observed, the gains are modest, for the most part. Thus, a great need still exists for a method to improve motor function further.

Current rehabilitation techniques do not sufficiently restore lost function in many individuals. Statistically significant improvements to motor deficits can be induced even several months after stroke. However, these improvements do not consistently improve quality of life for the vast majority of patients and their caretakers, thus greater improvements in motor skills are needed following rehabilitation.

Motor therapies typically involve practicing either fine motor or gross motor skills. Repetition is generally the mechanism of the therapies. In some variations, such as constraint therapy and mirror therapy, other mechanisms are engaged.

Some examples of typical motor therapies may be actions such as: squeezing a dynamometer, turning on/off a light switch, using a lock and key, opening and closing a door by twisting or depressing different doorknobs, flipping cards, coins and other objects over, placing light and heavy objects at different heights, moving pegs to hole and remove pegs from hole, lifting a shopping basket/briefcase, drawing geometric shapes, dressing, typing, reaching and grasping light and heavy objects, grasping and lifting different (size, shape, and texture) objects, doing a precision grasp, writing, drawing connect the dots, opening and closing a jar or medication bottle, lifting an empty and full cup/glass, using feeding utensils, cutting food, stirring liquids, scooping, pouring a glass of water with the paretic hand; or using the paretic hand to stabilize the glass and pouring with the good hand, picking an object and bring to target, using a spray can, cutting with scissors, or brushing teeth/hair.

U.S. Pat. No. 6,990,377 (Gliner, et al.) describes a therapy to treat visual impairments. The therapy includes presenting various types of visual stimuli in conjunction with stimulation of the visual cortex. The therapy described in Gliner does not control the timing relationship of the stimuli and the stimulation.

U.S. Patent Application Publication 2007/1079534 (Firlik, et al.) describes a therapy having patient interactive cortical stimulation and/or drug therapy. The therapy has patients performing tasks, detecting patient characteristics and modifying the stimulation depending on the detected patient characteristics. The therapy described in Firlik does not control the timing relationship between the tasks and the cortical stimulation.

It is common in the prior art to suggest that stimulation of the cortex, the deep brain, the cranial nerves and the peripheral nerves are somehow equivalent or interchangeable to produce therapeutic effects. Despite these blanket statements, stimulation at different parts of the nervous system is not equivalent. It is generally understood that the vagus nerve is a nerve that performs unique functions through the release of a wide array of neuromodulators throughout the brain. To generate certain kinds of plasticity, the timing of the stimulation of the vagus nerve is critical in producing specific therapeutic effects.

U.S. Pat. No. 6,104,956 (Naritoku, et al.) is representative of work done using vagus nerve stimulation (VNS) to treat a variety of disorders, including epilepsy, traumatic brain injury, and memory impairment. The VNS is delivered without reference to any other therapy. To improve memory consolidation, VNS is delivered several minutes after a learning experience. Memory consolidation is unrelated to the present therapy for treating motor deficits.

SUMMARY

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

In an embodiment, the disclosure includes a method of treating motor deficits in a stroke patient, comprising assessing a patient's motor deficits, determining therapeutic goals for the patient, based on the patient's motor deficits, selecting therapeutic tasks based on the therapeutic goals, performing each of the selected therapeutic tasks repetitively, stimulating the vagus nerve of the patient during the performance of the selected therapeutic tasks, and improving the patient's motor deficits.

In a second embodiment, the disclosure includes a method of treating motor deficits in a stroke patient, comprising assessing a patient's motor deficits, determining therapeutic goals for the patient, based on the patient's motor deficits, selecting therapeutic tasks based on the therapeutic goals, performing each of the selected therapeutic tasks repetitively, observing the performance of the therapeutic tasks, initiating the stimulation of the vagus nerve manually at approximately a predetermined moment during the performance of the therapeutic tasks, stimulating the vagus nerve of the patient during the performance of the selected therapeutic tasks, and improving the patient's motor deficits.

In a third embodiment, the disclosure includes a method of treating motor deficits in a stroke patient, comprising assessing a patient's motor deficits, determining therapeutic goals for the patient, based on the patient's motor deficits, selecting therapeutic tasks based on the therapeutic goals, performing each of the selected therapeutic tasks repetitively, detecting the performance of the therapeutic task, automatically initiating vagus nerve stimulation at a predetermined moment during the detected performance of the therapeutic task, stimulating the vagus nerve of the patient during the performance of the selected therapeutic tasks, and improving the patient's motor deficits.

In a fourth embodiment, the disclosure includes a system for providing therapy for a motor deficit, comprising, an implantable stimulation system including an implantable pulse generator (IPG), lead and electrodes to stimulate a patient's vagus nerve, a clinical controller with stroke therapy software, an external communication device to communicate between the clinical controller and the implantable stimulation system, and a manual input device, coupled to the clinical controller, wherein the manual input device is engaged during performance of a therapeutic task causing the clinical controller to send a signal using the external communication device to the implantable stimulation system, so that a patient's vagus nerve is stimulated during the performance of the therapeutic task.

In a fifth embodiment, the disclosure includes a system for providing automated therapy for a motor deficit, comprising, an implantable stimulation system including an IPG, lead and electrodes to stimulate a patient's vagus nerve, a clinical controller with stroke therapy software, an external communication device to communicate between the clinical controller and the implantable stimulation system, and a motion detection system, coupled to the clinical controller, wherein the motion detection system detects performance of a therapeutic task and at a predetermined time during the therapeutic task causing the clinical controller to send a signal using the external communication device to the implantable stimulation system, so that a patient's vagus nerve is stimulated during the performance of the therapeutic task.

These and other features may be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents. The present application describes several embodiments, and none of the statements below should be taken as limiting the claims generally.

Where block diagrams have been used to illustrate the embodiments, it should be recognized that the physical location where described functions are performed are not necessarily represented by the blocks. Part of a function may be performed in one location while another part of the same function is performed at a distinct location. Multiple functions may be performed at the same location. In a functional block diagram, a single line may represent a connection, in general, or a communicable connection, particularly in the presence of a double line, which may represent a power connection. In either case, a connection may be tangible, as in a wire, or radiated, as in near-field communication. An arrow may typically represent the direction of communication or power although should not be taken as limiting the direction of connected flow.

Therapy

VNS is paired with a motor therapy by providing the stimulation at some time during the motor therapy, for example, the beginning of the motion. Because the cortical plasticity is generated by the stimulation for a short time period, as short as a few seconds, the VNS should be provided so that most of the VNS is during the motions that constitute the therapy.

Figure 1:
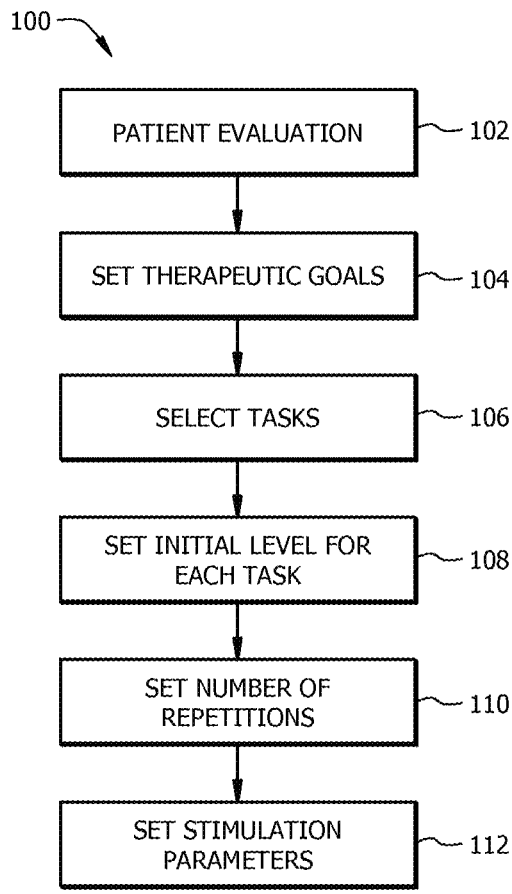
FIG. 1 is a flowchart depicting a task selection and therapy parameter selection process for a paired-VNS motor therapy, in accordance with an embodiment.

With reference to FIG. 1, a flowchart 100 depicts a task selection and therapy parameter selection process for a paired-VNS motor therapy 100, in accordance with an embodiment. The process 100 begins with a patient evaluation at 102. The patient evaluation may include a standard medical evaluation, medical history, and assessment of the patient's motor deficit. Persons of ordinary skill in the art are aware of other information that can be included in a patient evaluation. The patient's motor deficit or handicap may be assessed using standard motor deficit assessment criteria, such as Fugl-Meyer, Barthel Index, Box and Block Test, Canadian Occupation Performance Measure (COPM), Functional Independence Measure (FIM), Motor Assessment Scale (MAS), Action Research Arm Test (ARAT), Modified Rankin Scale, Nine hole peg test, NIH Stroke scale, Stroke Impact Scale (SIS) or any other appropriate assessment measures.

The process 100 may continue with setting the therapeutic goals at 104. Therapeutic goals may include such things as tying shoes, unlocking doors, eating, or performing other basic life tasks. Persons of ordinary skill in the art are aware of other types of goals.

Taking into consideration the therapeutic goals, a set of tasks are selected at 106 that either address specific muscle groups necessary to achieve the therapeutic goals, mimic the basic life tasks, or mimic some portion of those tasks. For example, if the goal is to be able to unlock a door, then the task of inserting a key and turning the key in a lock may be selected as a task. On the other hand, if the patient is suffering from more serious disabilities in this regard, then the task of reaching and grasping an object may be selected, as a first step toward the task of unlocking a door.

Tasks may include: Reach and grasp; Lift objects from table; Circumduction and bimanual tasks (mainly involving wrist and distal joints); Stacking objects; Slide credit card in slot; Turning on and off light switch; Squeezing objects; Writing; Typing; Stirring liquid in a bowl (bimanual); Dial a cell phone (bimanual); Fold towels or clothes (bimanual); Wear a belt; Tying shoelaces; Eating; Brushing teeth; Combing hair.

Each of the tasks is defined with a spectrum of levels. The task of moving a weight, for example, may include smaller weights and larger weights. Given a patient's abilities and the therapeutic goals, the initial task level is selected at 108. The patient may begin performing the task at the selected level. As the therapy proceeds, the level of the task may be changed to reflect changes in the patient's ability to perform the task. If a patient becomes adept at performing a task at the selected level, the level may be increased. If the patient struggles to perform the task at a given level, the level may be decreased.

Each task may be repeated many times. In a typical therapy, a task may be repeated from about 30 to about 50 times in a session. The number of repetitions for each task is selected at 110. The stimulation parameters for the vagus nerve stimulation, such as the amplitude, pulse width, the duration of the pulse train, frequency, and train period are selected at 112.

Figure 2:
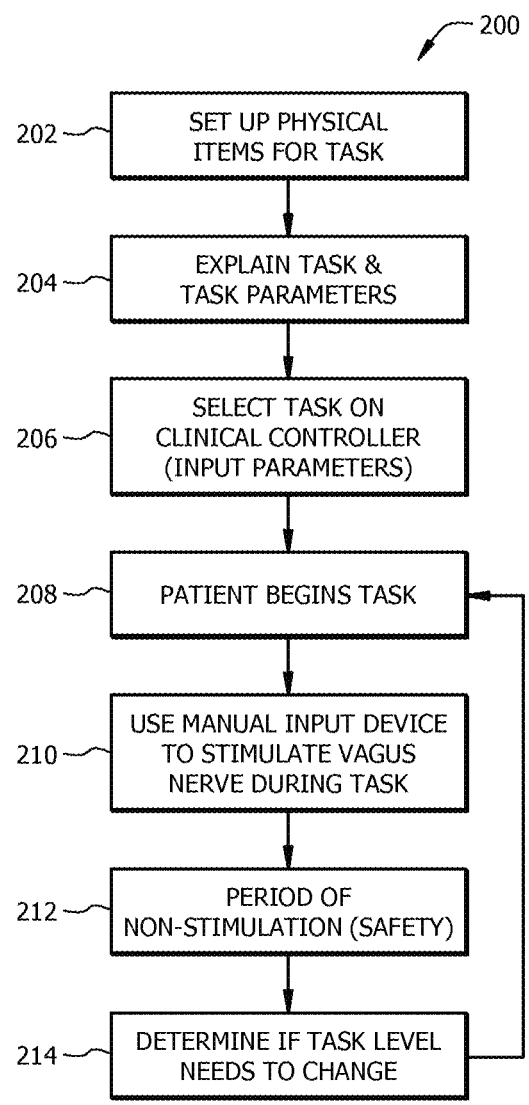
FIG. 2 is a flowchart depicting a setup and administration process for a paired-VNS motor therapy, in accordance with an embodiment.

With reference to FIG. 2, a setup and therapy delivery process 200 is shown. The physical items necessary for a selected task may be setup in the appropriate therapy space at 202. The task and task parameters, such as what counts as success, are explained to the patient at 204. The task delivery software is used to control the delivery of stimulations and to record data at 206. When the patient is instructed that the therapy has begun, the patient performs the first selected task at 208, in accordance with the instructions given. At approximately a determined point in the performance of the task, the manual input device is used to cause the vagus nerve of the patient to be stimulated at 210. Typically, the vagus nerve is stimulated with a 500 millisecond pulse train at approximately 0.8 milliamperes. The 500 millisecond duration has been selected as sufficient to generate directed plasticity. Experiments have shown that a 500 millisecond stimulation generates directed plasticity that lasts less than 8 seconds. While longer pulse trains may be effective, the shorter duration is typically preferred because the shorter stimulation leads to less side effects. Following stimulation at 212, there is a period of non-stimulation, which may be at least as long as the preceding period of stimulation. The period of non-stimulation may be a safety measure and may be part of the therapeutic process. When the task has been completed, the task level may be evaluated at 214, to determine if the task level is too simple or too advanced for the patient. The task level may be changed at this point, as appropriate. The patient then performs the task again at 208 until the task has been repeated a predetermined number of times.

Figure 3:
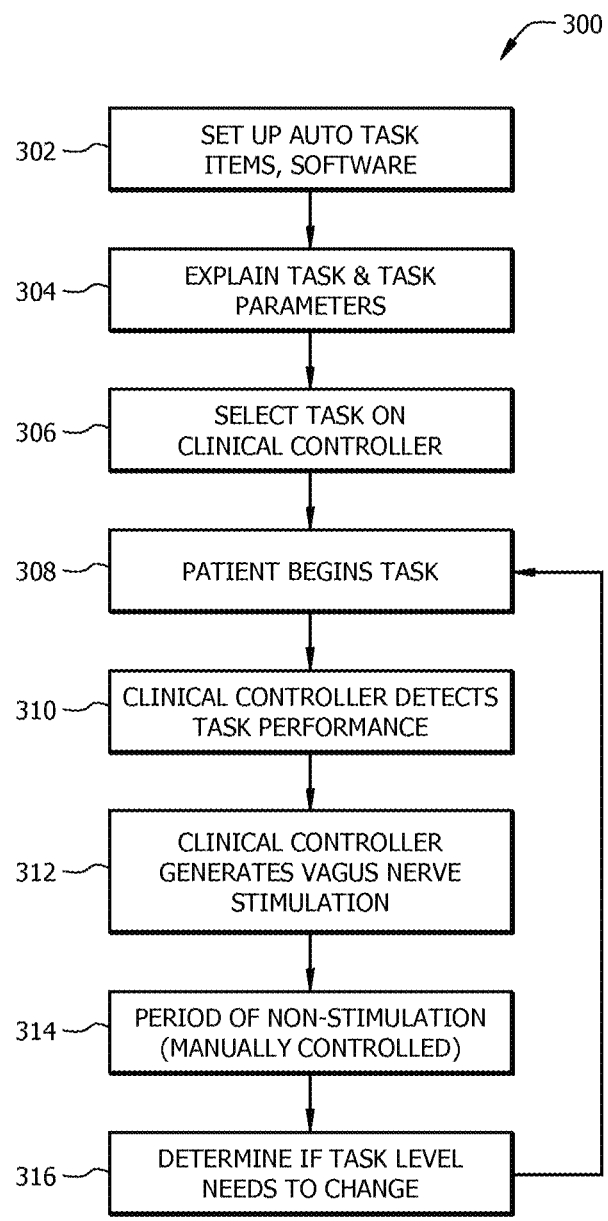
FIG. 3 is a flowchart depicting another setup and administration process for an automated paired-VNS motor therapy protocol, in accordance with an embodiment.

With reference to FIG. 3, a setup and automated therapy process 300 is shown. The physical items necessary for a selected task may be setup in the appropriate therapy space at 302. The setup may include initiating software to administer the automation. The task and the task parameters, such as what counts as success, are explained to the patient at 304. The task delivery software is used to control the delivery of stimulations and to record data at 306. When the patient is instructed that the therapy has begun, the patient performs the first selected task at 308, in accordance with the instructions given. A clinical control device detects task performance at 310. Cameras or other sensors may be used for to detect the patient's movements. At a determined point in the performance of the task, the control device causes the vagus nerve of the patient to be stimulated at 312. Following stimulation, there is a period of non-stimulation at 314, which may be at least as long as the preceding period of stimulation. The period of non-stimulation may be a safety measure and may be part of the therapeutic process. When the task has been completed, the task level may be evaluated at 316, to determine if the task level is too simple or too advanced for the patient. The task level may be changed at this point, as appropriate. The patient then performs the task again at 308 until the task has been repeated a predetermined number of times.

Figure 4:
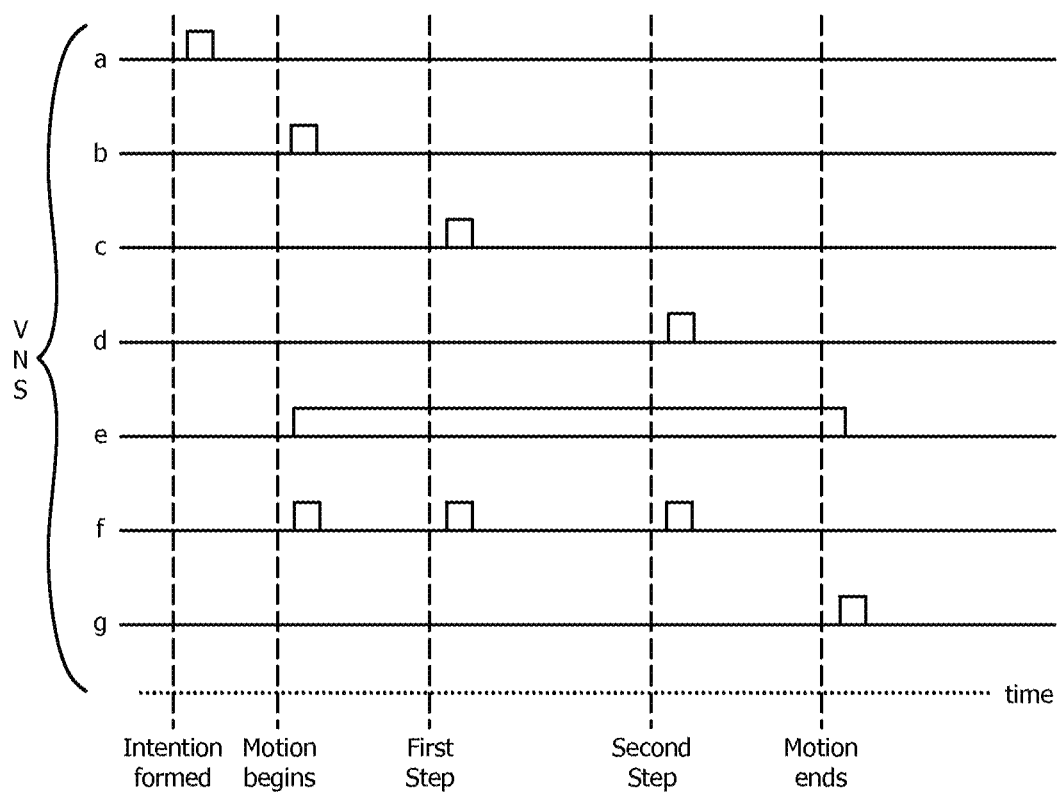
FIG. 4 is a graph depicting the timing of a therapeutic motion and examples of possible stimulation timing variations for paired VNS.

With reference to FIG. 4, a graph depicts the timing of the therapeutic task and examples of vagus nerve stimulation timing. Before a motion begins, the patient forms a mental intention and soon after, the motion begins. The task may typically include a series of motions. For example, a task may include, reaching, grasping, moving, releasing, and returning. Between each of these motions is a transition point or step that may be used to time the stimulation. Finally, the motion ends.

The vagus nerve stimulation may be effectively delivered at various times during the therapeutic task. For example, line a shows a vagus nerve stimulation given after the intention to move is formed and before the motion begins. Line b shows a vagus nerve stimulation delivered after the motion begins. Line c shows a vagus nerve stimulation delivered after a first transition point or step in the therapeutic task. Line d shows a vagus nerve stimulation delivered after a second transition point or step in the therapeutic task. Line e shows a longer vagus nerve stimulation delivered between the time the motion starts and shortly after the motion ends. The extended stimulation duration shown at line e may be a single long pulse train or a series of half-second pulse trains. Line f shows three vagus nerve stimulations delivered during the therapeutic task, after the motion begins, after the first step and after the second step. Any of these VNS delivery methods may be used singularly or in combination.

Other systems may be used to monitor movements, so that appropriate VNS timing can be determined. For a wrist flexion, we might use a camera to model the movement as a wire frame (e.g., bones with joints) and compare the movement to past attempts and to optimal (e.g., normal) movement in order to find the best movements that the patient can generate. Movements, such as walking, grasping or tying, may be quantified as location, direction, speed, and angle of each joint as a function of time. For speech production, vocalizations might be compared to previous sounds and normal speech sounds produced by others. Vocal movements might be quantified based on the intensity, duration, pitch, formant structure (vowels), formant transitions (consonants), voice-onset time, and other standard methods of quantifying speech sounds.

Selecting the appropriate paired VNS period depends on the nature of the motion and the equipment used to provide the pairing timing.

VNS could also be delivered during the planning stages before movement begins. This usually takes only a few hundred milliseconds but can be extended by giving a sensory cue that instructs the subject what motion needs to be done followed by a trigger cue some seconds later telling them when to begin the movement. This strategy makes it possible to specifically pair VNS with motor planning, which is an important part of motor control.

VNS may be paired with the best movements in order to shape future movements to be smooth and efficient (e.g., avoid spasticity, tremors, co-contraction of opposing muscles, or the use of muscles that would not normally be used to accomplish the task). VNS could also be delivered after the movement is completed and determined to be effective (e.g., the best movement of the attempts occurring in the last about 30 seconds).

Thus, VNS could be delivered before, during, or after movement. A measurement may show that the movement will be, is, or was effective (e.g., acceptable or better than average). Pairing may mean temporally associated with, not necessarily simultaneous. For the rat study discussed below, all VNS was delivered after the end of the target movement. However, in many cases, the rats continue with the movement after the target movement is achieved such that VNS is sometime delivered while the rat is moving.

VNS may be paired with supervised, massed practice movement therapy three times per week. The duration of the therapy may be six weeks. The duration of each therapy session may be approximately one hour. The therapist may determine each session's therapy tasks to progress toward the Canadian Occupational Performance Measure (COPM) goals established at the intake evaluation. Goals may focus on upper limb rehabilitation—most tasks may typically require four movement components: reaching, grasping, manipulating, and releasing an object. During each session the 'primary therapy principles' may be used to guide the development of the tasks to be performed each day. Prior to each therapy visit, the therapist team may meet and develop the task plan, ensure available materials and determine the plan to increase and decrease difficulty to and determine a realistic number of repetitions to be set as a goal.

The therapy implements several principles. The first principle is task specificity. Improvement of a motor skill requires practice of the movement; thus, each task may include components of reach, grasp, manipulate, and release specifically related to the target task.

Another therapy principle is that of repetition. Large numbers of repetitions of each task is required to master a motor skill, so the goal for therapy is to perform from about 30 to about 50 repetitions of a given task in a one-hour session (about 120—about 200 total repetitions per session). The focus of each therapy session may involve from about 3 to about 5 tasks in order to achieve the high numbers of repetitions.

Another therapy principle is active engagement. Optimal learning occurs with high levels of motivation and engagement. Thus, participants may help to set goals, therapists may make it clear how the target task relates to each goal, task practice may be varied to minimize boredom, and the task may be constantly adapted to require active engagement and effort to complete.

Another therapy principle is massed practice. Within a session, massed practice promotes better learning than distributed practice. Thus, the therapeutic environment needs to allow continuous repetition. For example, therapist may line up 10 objects in a row to allow for continued repetition. Rest breaks are given only if requested by the patient or required by the VNS.

Another therapy principle is variable practice. Variable practice can be important for learning transfer. The movement components may stay the same, and the context of the components may change between trials or sessions.

The therapy session should consist of from about 3 to about 5 tasks to allow variability and patient engagement. A reach & grasp task may be included in each session. The majority of patients need work in this area, so including it as a required task allows for consistency between patients and useful in judging rehabilitation with assessments.

The therapy session may, at least initially, take place under the supervision of one or more therapists. The patient may perform the action without assistance from the therapist. The therapist may manually deliver the VNS trigger during the "key" part of the movement that is being trained (typically when the subject touches or is about to touch the object during the reach). Alternatively, automatic delivery could be used. Tasks may be appropriately graded to require processing and effort by the patient but some degree of success. As a general guideline, if the patient is unable to complete the task successfully after approximately five attempts, it should be downgraded in difficulty. This guideline may be superseded by the therapist's clinical judgment regarding the patient's motivation, ability, and fatigue. If the patient is able to complete the task with little difficulty approximately (e.g., from about 10 to about 20 times) it should be upgraded in difficulty. If they can complete it, but it is slower than normal, then it is still a challenging task, and variety may need to be introduced to alleviate boredom.

The upgrading and downgrading of tasks is dependent on the patient's goals as well as the effort required. The level of strength and endurance required for the goal is also an important consideration. For some patients, even higher repetitions may be required to achieve the endurance needs. The goal for repetitions of each task may be set ahead of time by the therapist and communicated to the patient.

Grading of tasks can involve several different components: Physical position of the patient. The patient may be standing to introduce variety, add endurance, and add balance components to the task performance. Alternatively, the patient may be sitting.

The position of the task materials may be changed. The height of the task materials may be changed. The depth of the task materials, placing the materials further away from patient, may be changed. The degree from midline of objects (left, midline, or right) may be varied. The weight of task materials may be changed. The size of the objects may be changed.

Adaptive equipment/materials may be used. A DYCEM mat may be used to prevent an item from sliding. The therapist may hold item to stabilize it. Materials may be used to increase the grip of a small object to match ability (e.g., use foam to build up a pen to make it easier to grasp).

The speed of task movement may be changed. A certain number of repetitions per minute may be implemented to focus on the speed of movement. The patient may be encouraged to slow down task performance The stability of the object may be changed. The object to grasp may be stable. The object to grasp may be moving (e.g., a ball is rolling on a table). The object may be placed on slippery surface or a sticky surface.

The same task can be practiced with different forms of material to achieve variety but still maintain high levels of repetition of the overall task. For example, to work on grasp and release of small objects, a plethora of everyday objects could be used, such as coins, paperclips, credit cards, cell phones, etc.

Task performance may be monitored by the therapist, and each VNS stimulation may be recorded by the software and presented to the therapist as a visual counter on the screen.

If in the therapist's assessment there are other rehabilitation issues that may require intervention, such as restricted range of motion, this can be addressed outside of the about one hour motor practice or addressed prior to the start of the VNS therapy. If there are significant non-motor impairments, such may disqualify the participant.

Patients may not be given a home exercise program of specific items to practice. However, they may be told to participate in their normal every day activities and be encouraged to "practice using your impaired upper extremity as much as possible".

Examples of Goal and Task Grading

Example 1: Grasp and Release. The patient's goal is to be able to unload dishwasher. The target task involves the ability to grasp, manipulate, and release a variety of objects along with a variety of strength and range of motion requirements and some degree of endurance (e.g., being able to stand for the entire duration).

Materials: spoon, fork, knife, large serving spoon, large and medium mixing bowl, coffee mug, drinking glass, small plate, large dinner plate, a DYCEM mat, foam.

Method: First, Patient sits at table with objects at midline Second, for each task repetition, the patient reaches out to grasp object and place on shelf about six feet above the table. Third, 10 objects are lined up to allow continuous repetition of the movement and achieve high numbers.

Grading: The task can be upgraded in difficulty by: challenging patient that a certain number of repetitions be completed in one minute; using a variety of sizes instead of the same size/shape in a row; requiring the patient stand to perform; requiring the patient bend down to retrieve the object; requiring the patient reach higher to place the object; requiring the patient sort and place each object in the correct position in a drawer; mixing bilateral lifting with single hand tasks; silverware is placed in a basket to be removed from; weight baring is required in one limb to stabilize during a task (e.g., the patient leans on his less affected arm and practices wiping the table with the impaired arm); and/or including bilateral tasks that aren't symmetrical (e.g., the patient uses a spray bottle with the impaired hand and cleans with the less affected arm).

The tasks can be downgraded in difficulty by: wrapping the object in foam to make it easier to grasp; placing objects on a DYCEM mat to minimize slipping; requiring object be moved from impaired hemifield to less impaired hemifield; and/or performing bilateral tasks.

Introducing variety and still achieving high numbers of repetitions. First, the goal for this task is 200+ repetitions. Since the goal is a complex task that involves several components this may be the only task performed is this session. Second, for the first part of the session, the task may be designed to primarily challenge the grasp. The individual may grasp objects in a variety of challenging ways with less challenge focused on the reach or manipulate aspect of the entire task, for 100 repetitions (e.g., 10 objects×10 repetitions) This may take about 25 minutes. There is a line of objects set up, thus there may be very little rest between repetitions. The second part may have greater emphasis on the reach part of the task, but the task is still repeating the components. The individual may now pick up a relatively easy object, that is further away from him, requiring a reach to different aspects of the field in front of him. Each of these trials may take longer. He may perform 35 trials of this from a variety of reach locations, which may require approximately 15 minutes. For variety, the object could be close and the he would be required to reach at the limits of his ability for the release of the object. Finally, the third part may focus on manipulation and precision. For these trials, the initial grasp and reach is not as difficult, but the manipulation/release may be repeated, e.g. about 75 times in about 20 minutes. This may require precise placement of an object (e.g., the participant has to stack a set of spoons on top of each other or place cups in a precise stack. The day's session was focused on the goal with all repetitions were focused specifically toward the same task, but different aspects of the goal were emphasized to eliminate boredom and fatigue.

Example 2: Handwriting. The patient's goal involves being able to write checks and thank you notes.

Materials: pen, paper, pencil, dry erase board, cylindrical foam, sand tray, shaving cream, and tray.

Method: First, the patient sits at a table with a tray with a mound of shaving cream. Second, the patient practices spreading the cream evenly throughout the tray. Third, the patient practices free writing with a finger or with a stylus. Fourth, the patient practices loop drawing or free writing with writing utensil of choice. Fifth, the patient practices filling out forms or line writing within constrained box.

Grading: The tasks can be upgraded in difficulty by: increasing the number of words written (e.g., phone number, address, sentences); decreasing task difficulty by using built up writing utensils to aid in grip; and/or decreasing task difficulty by using dry erase board, shaving cream, writing large letters or loops.

Example 3: Bilateral activity. The patient's goal involves folding laundry.

Materials: 10 wash cloths, 10 hand towels, 10 bath towels, 10 t-shirts, 10 pairs of socks.

Method: First, the patient may sit or stand at the table. Second, the patient may fold towels at midline. Third, all towels may be folded in half and then in half again using bilateral upper extremities. Fourth, folded towels may be placed in laundry basket.

Grading: Tasks may be decreased or increased in difficulty by changing the size and weight of objects. Tasks may be decreased or increased in difficulty by changing the number of folds required in the object. Task can be increased or decreased in difficulty by changing the location of where the object is to be grasped or placed. The therapist may unfold the towels to allow rapid repeat of task.

Example 4: Fine motor tasks. The patient's goal involves fishing.

Materials: 10 fishing lures, various sized bobbers, fishing weights, fishing line, a tackle box, and a fishing reel.

Method: First, The tackle box is placed at the patient's midline. Second, fishing weights bombers and lures are placed on the affected side. Third, the patient is instructed to pick up items and place them in the top box. Fourth, the patient is instructed to pick up items one at a time. Fifth, the patient practice is tying a fishing line. Sixth, the patient practices stabilizing the fishing rod with one hand and reeling with the other hand.

Grading: Increase or decrease task difficulty by increasing or decreasing the size of the items in the tackle box. Increase or decrease the difficulty by increasing or decreasing the weight of items at the end of the fishing line.

Example 5: A discrete, specific task. The patient's goal involves opening doors.

Materials: A set of experimental doors knobs with various types of locks, keys, and actual doors.

Method: First, the key is built up with foam or putty to allow easier grasp of the key. Second, the knobs/locks are placed at an easily accessible height to allow the patient to sit and perform the task. Third, actual doors are used and the patient has to fully open the door and walk through.

Grading: A variety of knob types are used requiring different aspects of grasp. The knobs/locks are placed at progressively more difficult positions. The actual doors are light or heavy.

Systems and Devices

Figure 5:
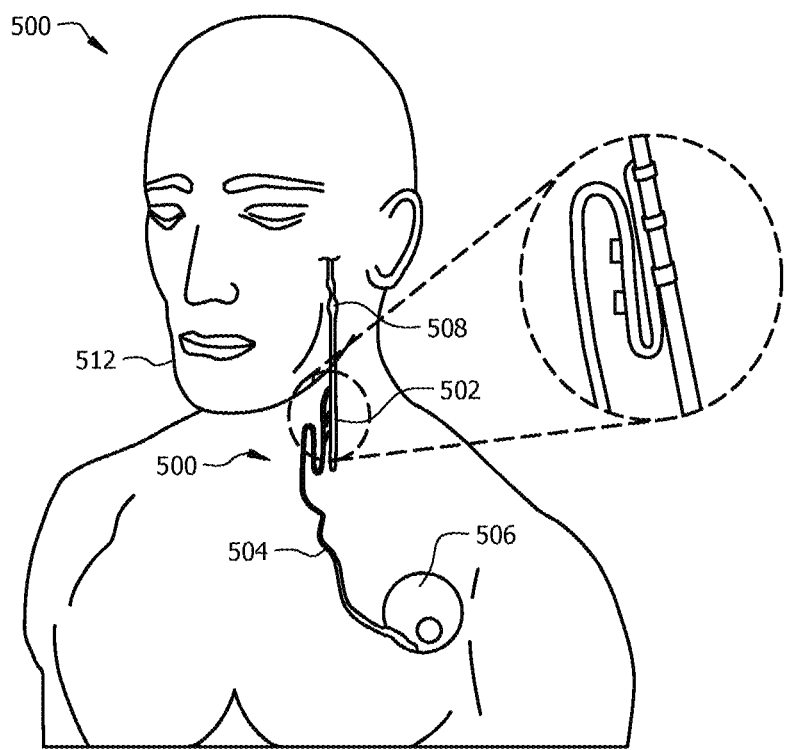
FIG. 5 depicts an implantable vagus nerve stimulation system, in situ, in accordance with an embodiment.

With reference to FIG. 5, an implantable vagus nerve stimulation system 500 is shown in situ. The implantable vagus nerve stimulation system 500 includes an IPG 506, electrodes 502, and a lead 504 connecting the IPG 506 to the electrodes 502. The IPG 506 may be implanted in the chest of a patient 512. The lead 504 travels below the skin to the neck of the patient 512. The electrodes 502 may be of the cuff-electrode type and may be attached to the left vagus nerve 508 in the neck of the patient 512. The IPG 506 sends electrical stimulation pulses through the lead 504 to the electrodes 502, causing stimulation of the vagus nerve 508. The IPG 506, lead 504, and electrodes 502 function similarly to the implantable vagus nerve stimulation systems commonly used in the treatment of epilepsy and as described in the parent patent application to this application.

Vagus nerve stimulation may be delivered with electrodes placed in direct contact (or proximate to) the left cervical vagus nerve, in the patient's neck. Other forms of stimulation may be used, including transcutaneous electrical or magnetic stimulation, physical stimulation, or any other form of stimulation. An example of a transcutaneous electrical stimulation system that could be adapted for use in the described therapy may be found in U.S. Pat. No. 7,797,042. Stimulation of the vagus nerve may be done at other sites along the vagus nerve and branches of the vagus nerve.

Figure 6:
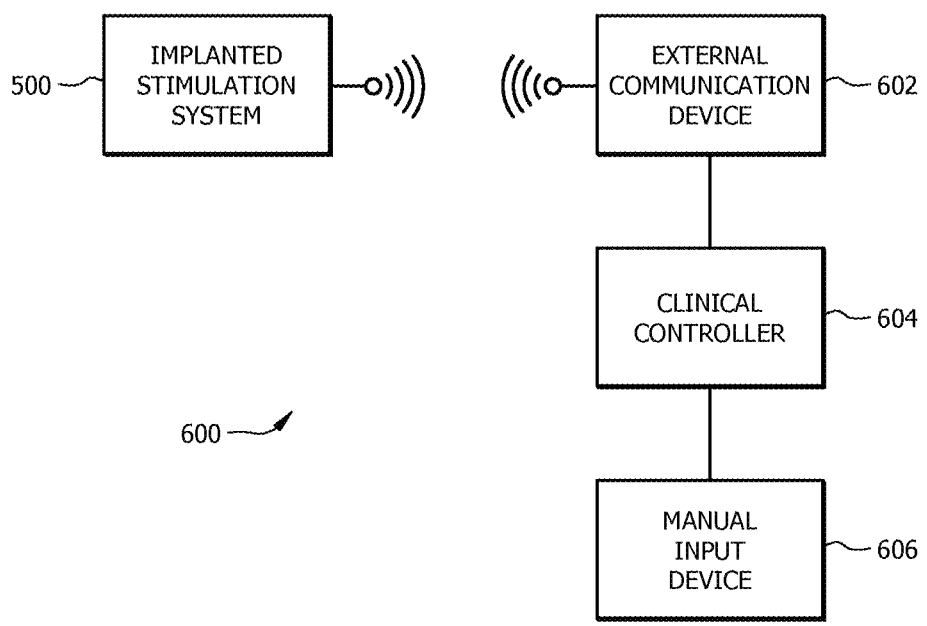
FIG. 6 is a functional block diagram depicting a paired-VNS motor therapy system including a manual VNS switch, in accordance with an embodiment.

With reference to FIG. 6, a stroke therapy system 600 is shown. The implanted stimulation system 500 communicates wirelessly with an external communication device 602. The external communication device is coupled to a clinical controller 604. The clinical controller 604 may be a computer, such as a laptop computer, running specialized paired VNS stroke therapy software. A manual input device 606 may be coupled to the clinical controller 604. The manual input device 606 may be a hand switch, a foot switch, a mouse button, or a keyboard key. When the manual input device 606 is switched or pressed, the clinical controller 604 sends a signal to the external communication device 602. The external communication device 602 sends a signal to the implanted stimulation system 500. The implanted stimulation system 500 receives the signal at the IPG 506 and generates stimulation of the vagus nerve at the electrodes 502.

Figure 7:
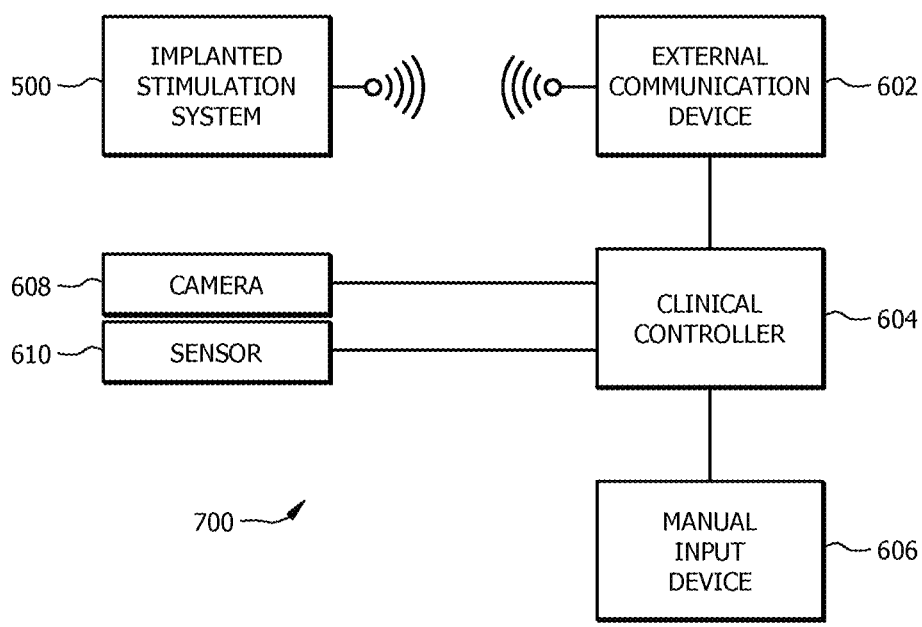
FIG. 7 is a functional block diagram depicting an automated paired-VNS motor therapy system, in accordance with an embodiment.

With reference to FIG. 7, a stroke therapy system 700 is shown. The implanted stimulation system 500 communicates wirelessly with an external communication device 602. The external communication device is coupled to the clinical controller 604, which may be coupled to manual input device 606. A camera 608 and sensor 610 may also be coupled to the clinical controller 604. The camera 608 and/or sensor 610 detect motion or attributes of the motion. The data detected by the camera 608 and/or sensor 610 are processed by the clinical controller 604. When the data indicates a threshold has been reached during the performance of the therapeutic task, the clinical controller 604 may send a signal to the external communication device 602, and the external communication device 602 may send a signal to the implanted stimulation system 500. The implanted stimulation system 500 receives the signal at the IPG and generates stimulation of the vagus nerve at the electrodes. The manual input device 606 may be used to control the delay between stimulations.

The system may also implement magnet mode, where a hand-held magnet may be swiped over the IPG in order to cause a stimulation. The specialized stroke software may include a magnet mode setting, to provide for use of this mode. When in magnet mode, swiping the hand-held magnet will deliver a pre-programmed stimulation (i.e. at whatever settings were programmed). The reason for this feature is the physician and patient do not need to be in proximity of the computer/external controller, an arrangement that may work better for some kinds of tasks. When not in magnet mode the magnet causes stimulation to stop, as a safety feature.

Figure 8:
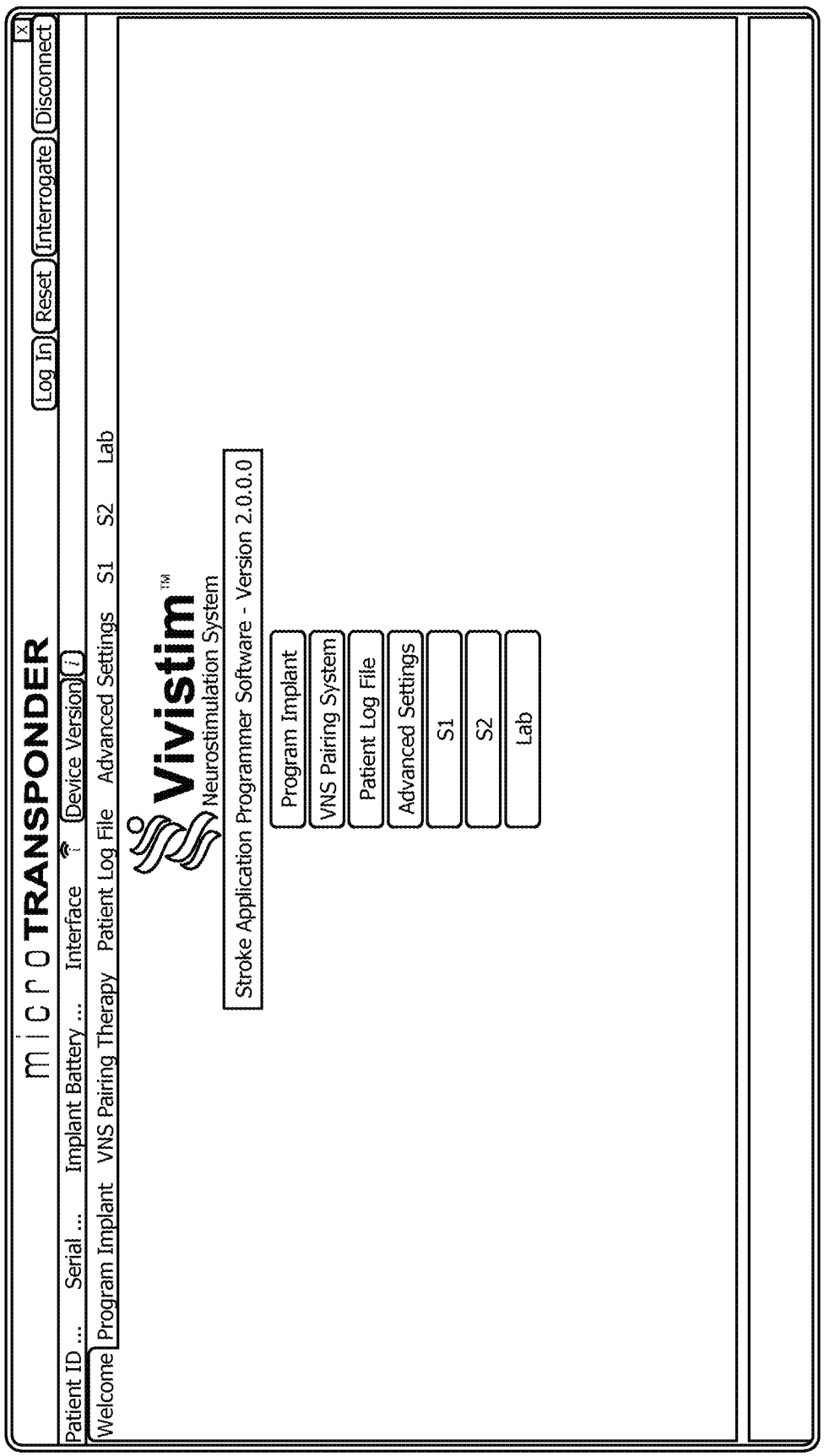
FIG. 8 is a screenshot of an initial interface screen, in accordance with an embodiment.
Figure 9:
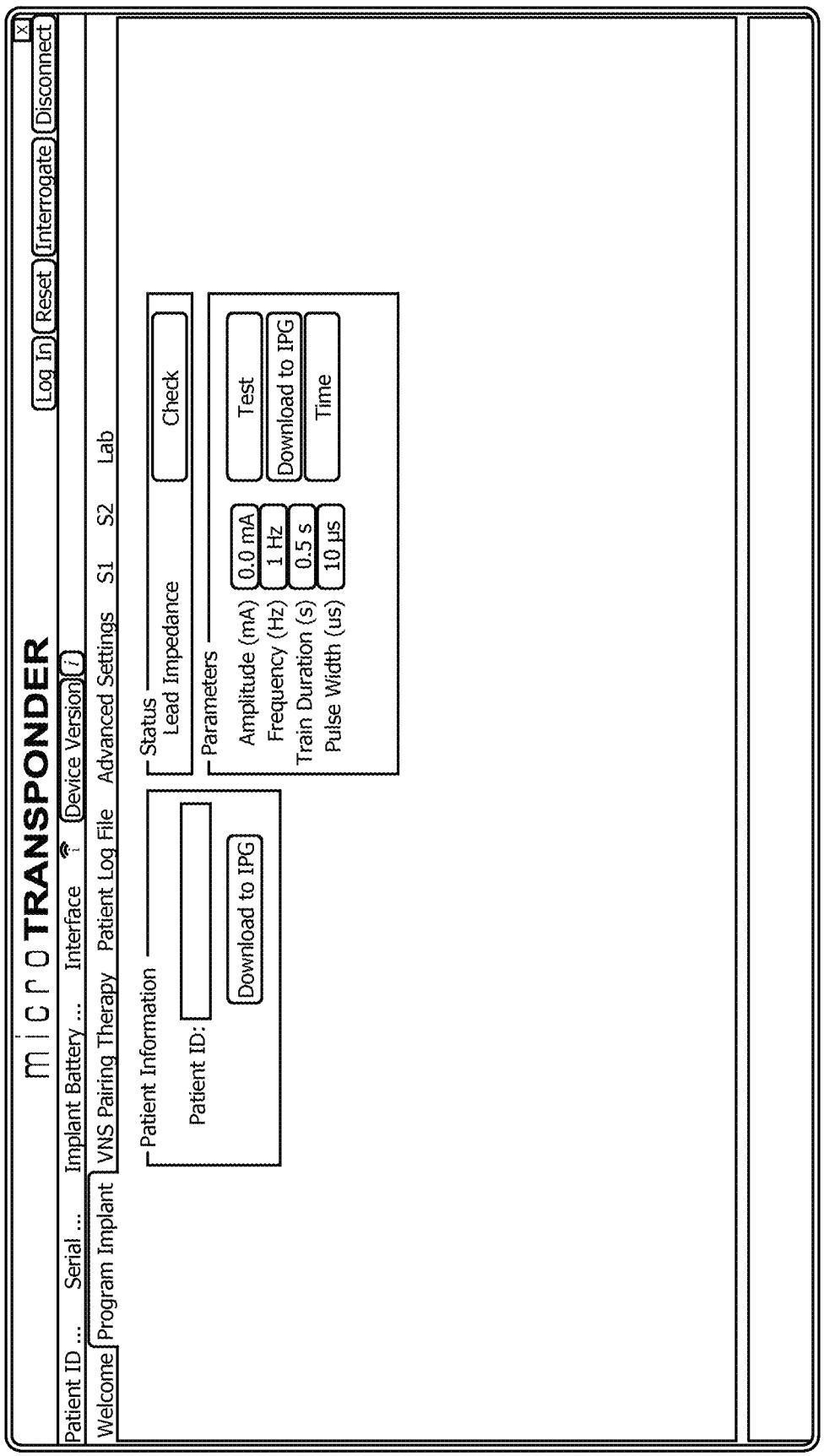
FIG. 9 is a screenshot of a therapy information screen, in accordance with an embodiment.
Figure 10:
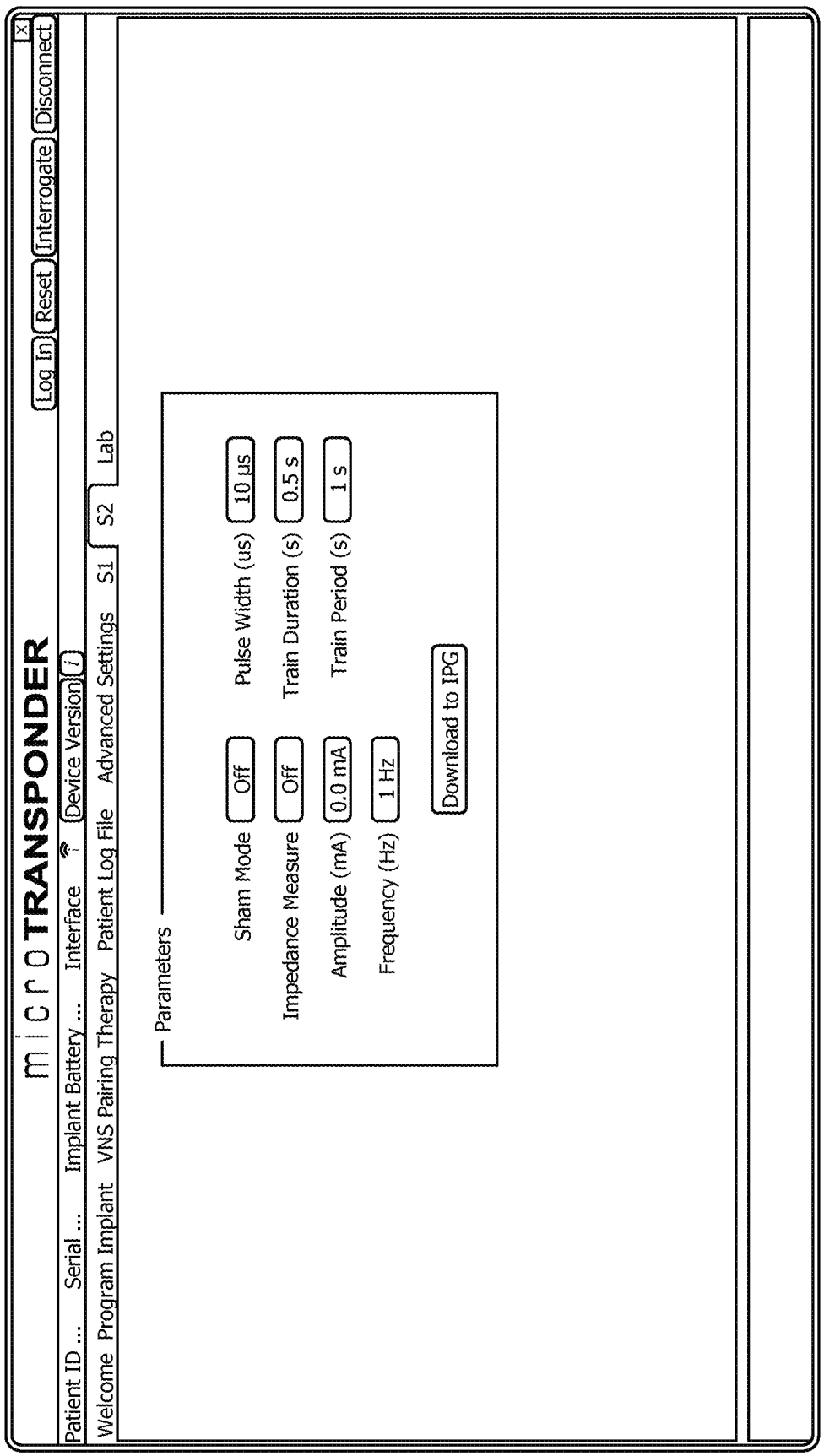
FIG. 10 is a screenshot of a stimulation parameter input screen, in accordance with an embodiment.
Figure 11:
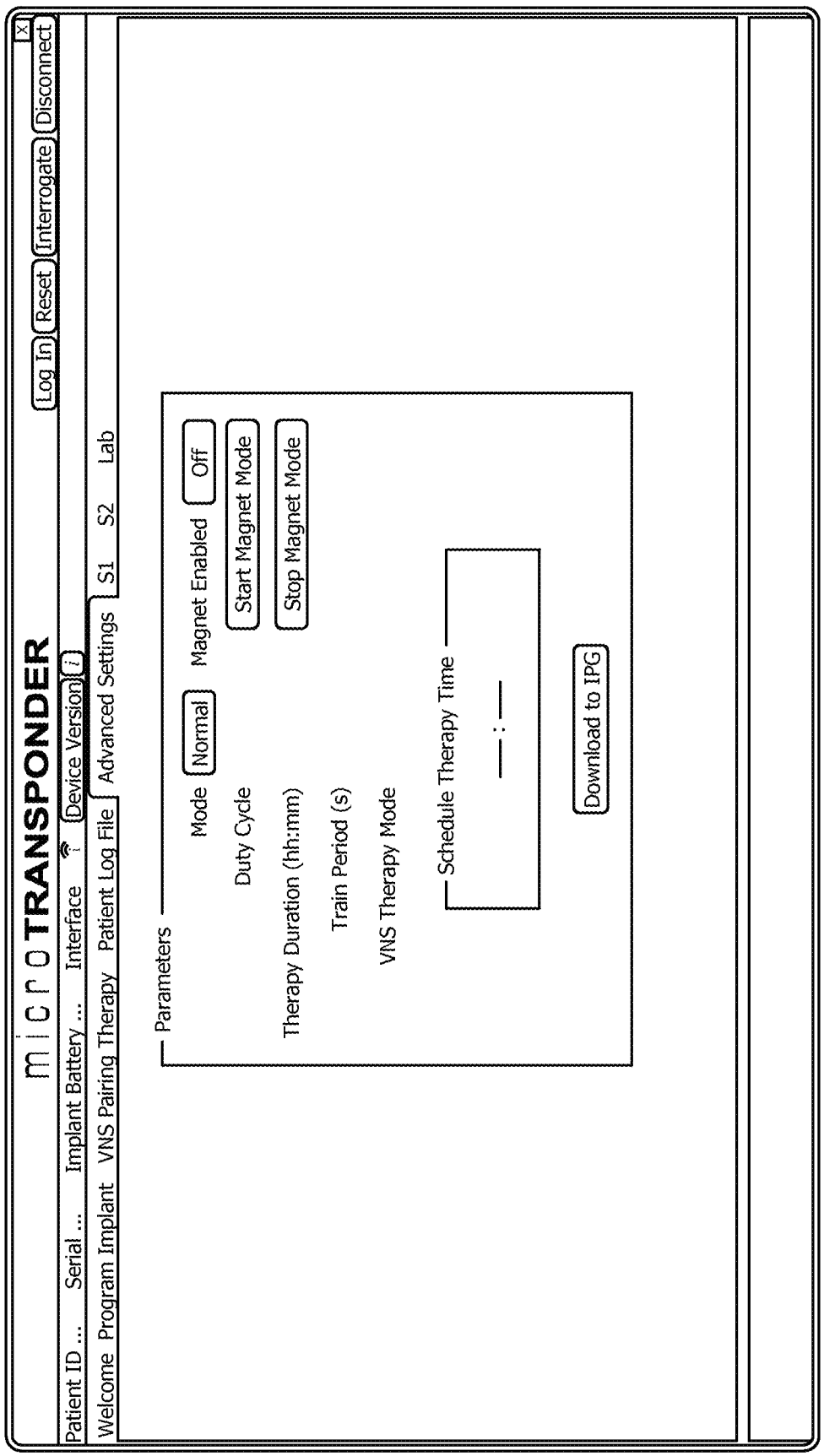
FIG. 11 is a screenshot of a therapy input screen, in accordance with an embodiment.
Figure 12:
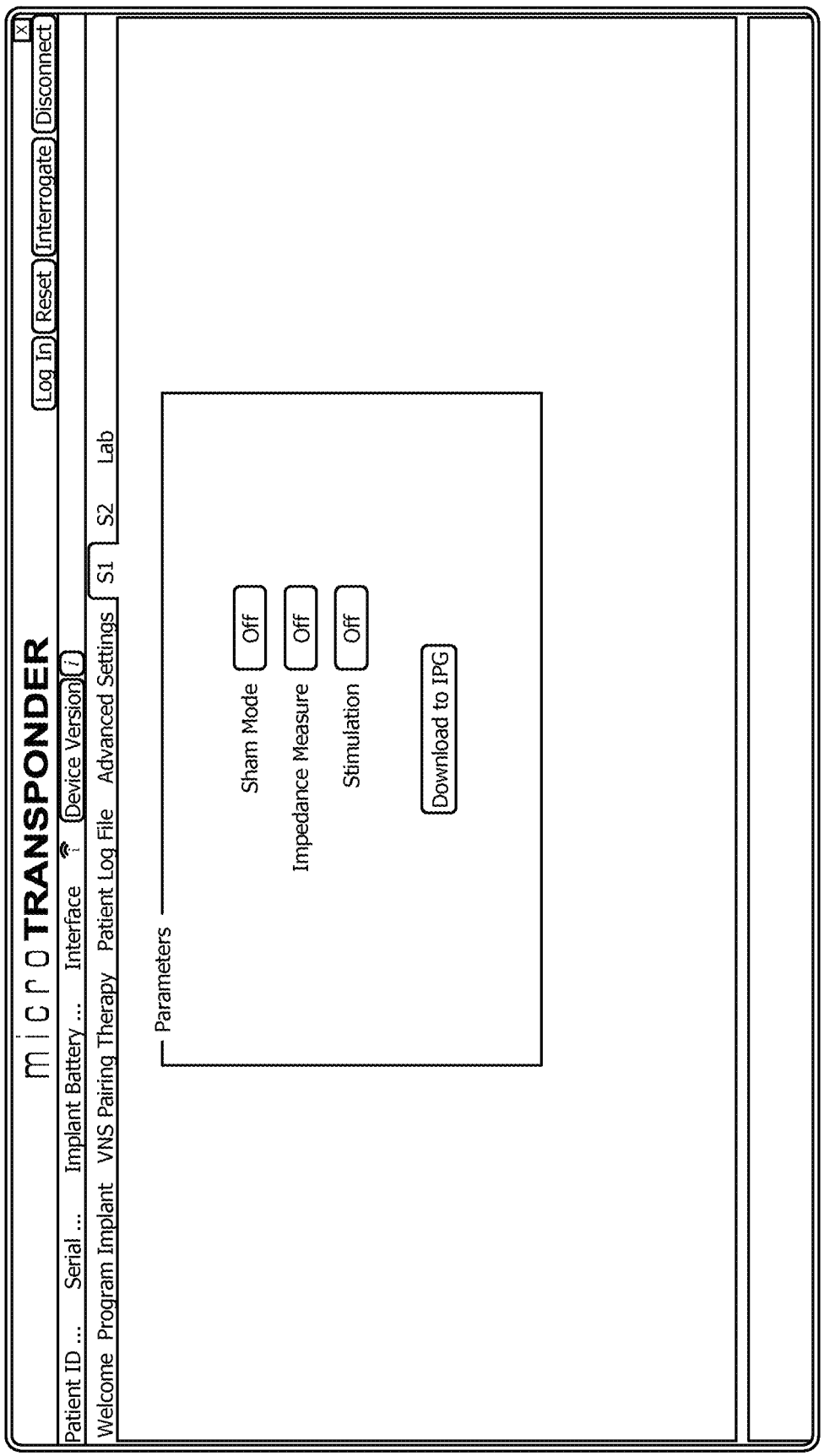
FIG. 12 is a screenshot of an IPG parameter input screen, in accordance with an embodiment.
Figure 13:
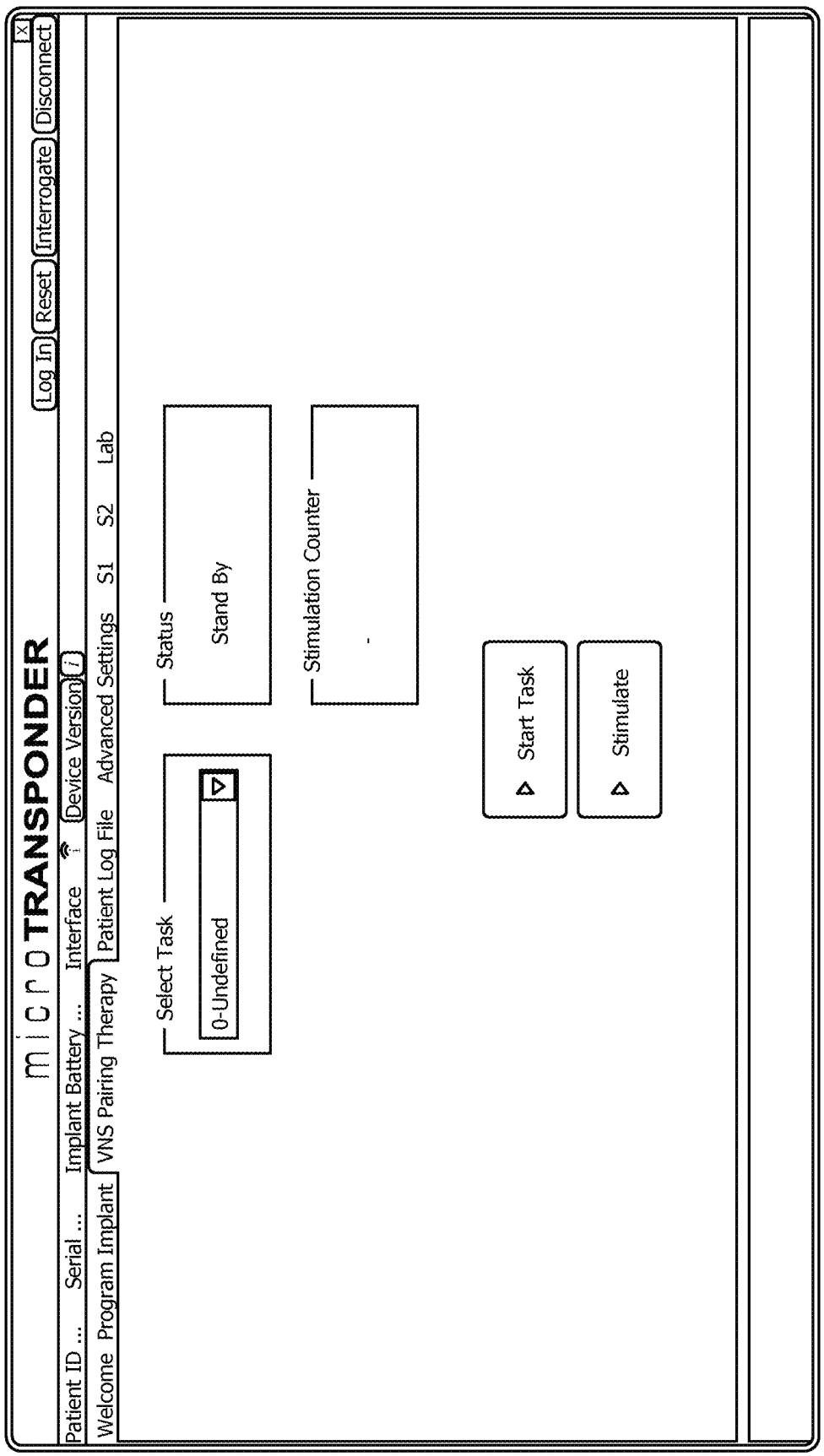
FIG. 13 is a screenshot of a therapy delivery screen, in accordance with an embodiment.

The clinical controller 604 may run specialized stroke therapy software. The specialized stroke therapy software manages patient data, controls the stimulations, sets the stimulation parameters, and records data from the therapy. FIGS. 8-13 show screenshots from an embodiment of the stroke therapy software. With reference to FIG. 8, a screen shot shows an initial page of the specialized stroke therapy software. The initial page allows the user to navigate to input screens for programming the implant, set the therapy parameters, and access patient data. With reference to FIG. 9, a screen shot depicts the input screen for programming the implantable system. With reference to FIG. 10, a screen shot depicts an input screen for further programming the implantable system. With reference to FIG. 11, a screen shot depicts an input screen for advanced settings. With reference to FIG. 12, a screen shot depicts an input screen for implantable parameters. With reference to FIG. 13, a screen shot depicts a therapy delivery screen. On the therapy delivery screen, a therapeutic task may be selected.

Figure 14:
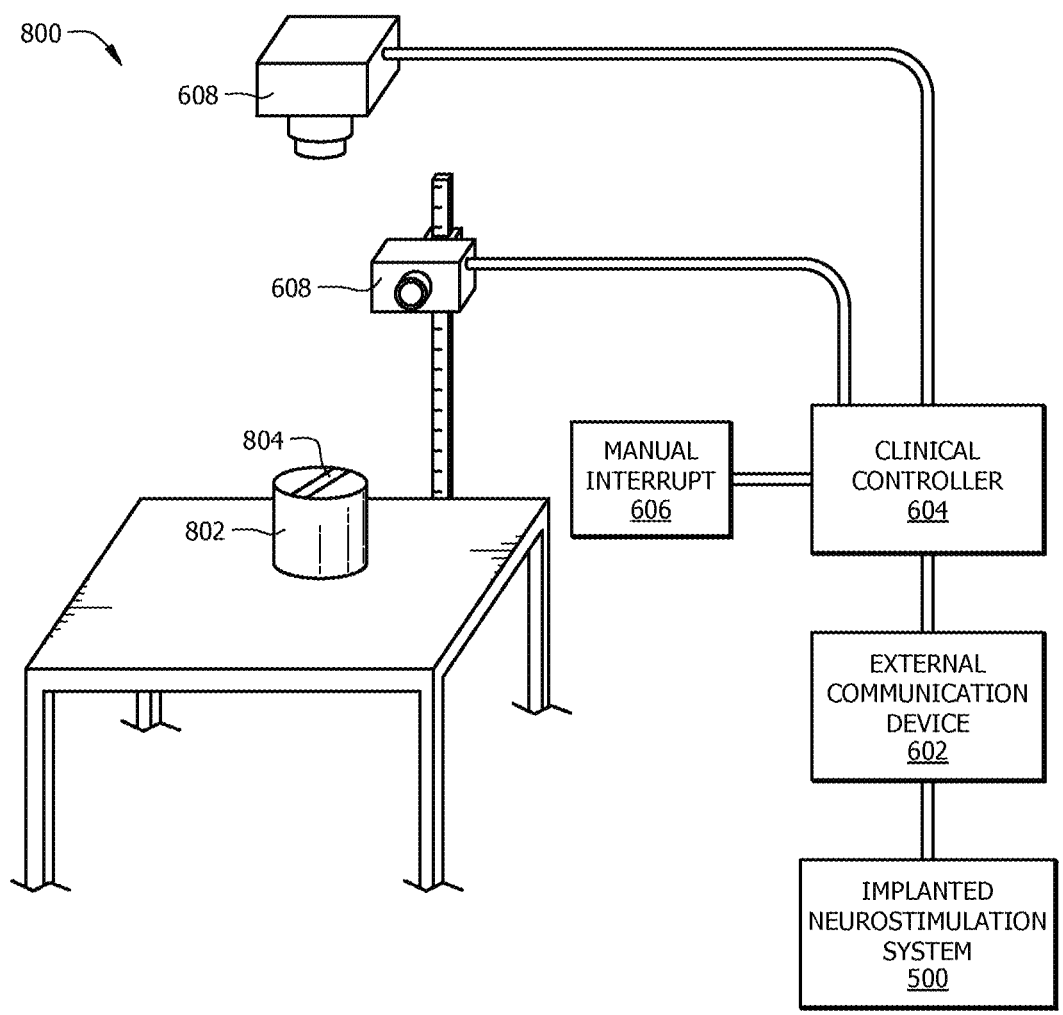
FIG. 14 is a schematic diagram of an automated pairing system, in accordance with an embodiment.

With reference to FIG. 14, an automated stimulation pairing system 800 is shown. One or more objects 802 such as a cylinder, a key, a block, or any other object suitable for manipulation-type tasks is placed in a workspace. Portions of the patient's body, such as a hand or fingers, may also serve as objects. The object 802 is marked with a colored marker 804 such as a piece of colored tape, a spot of paint, a colored sticker or any appropriate manner of marking an object with color. For some tasks, such as rotation, the colored marker 804 needs a long edge and a short edge, as shown. Any object 802 can be marked with a sticker or tracking sphere and tracked for the therapy. A camera 608 or a plurality of cameras 608 are placed around the workspace so that the object 802 and the marker 804 is within view of the camera 608. Cameras 608 may also be used to monitor the patient rather than an object or marker. In accordance with an embodiment, a camera may be placed above the workspace. The cameras 608 are connected to the clinical controller 604. Specialized software running on the clinical controller 604 uses data from the cameras 608 to determine the relative position, velocity, rotation or any other metric related to the performance of the given task. The clinical controller 604 uses the determined metric to decide when stimulation is appropriate and sends a stimulation signal to the external communication device 602. A manual interrupt 606 may be implemented so that a therapist can interrupt and control the rate of stimulation. The automated system 800 may be completely automated, in a closed loop setup so that the next stimulation is automatic. The automated system 800 may be arranged in an open loop fashion, so that the therapist must intercede before the next stimulation.

The specialized software monitors x, y, z translations of objects with an attached target. The specialized software includes parameters for a variety of tasks that may be performed using this type of closed loop automated system. Using a single camera and colored markers, a wide variety of tasks can be automated. Motion, speed, height, initiation of translation, acceleration, angular rotation, angular velocity, angular acceleration, force, velocity, acceleration, angular acceleration, path length, time to target, distance traveled to target, range of motion, height of object and combinations of these and other metrics can be used to trigger stimulation. Some example tasks include: slide a cup, lift a cup, spin a cup, Lift a cup and move it to some other location, move an object by rotating your wrist, turn a key, flip a coin, pick up a spoon. Tasks may be combinations of movements or tasks, such as lifting a cup and bring it to the mouth, lifting a penny and putting it on a shelf, lifting a key, putting it in a lock and turning the key, or sliding a cup to some point, picking it up, and spinning it 30 degrees. The tasks may be designed to isolate movements of specific muscle groups. Adaptive tracking of a base metric, based on past performance within a session or between sessions, can be used to generate improvement.

The automated paired stimulation system may be arranged so that when the object 802 is moved into or out of a pre-defined boundary that surrounds the object, vagus nerve stimulation is triggered.

A marker 804 can be placed on the patient's hand or arm rather than on an object.

When the object 802 when lifted or lowered in the z-axes i.e. towards the camera 608, the change in the area of the marker 804 may be detected and used to trigger stimulation.

The object 802 may be moved to specified places on the surface. For example, the task may require the patient to move the task object 802 to a square on the surface. When the object is successfully moved to the square, the VNS stimulation is triggered.

Stimulation is triggered during the movements. The specialized software may stimulate on the best trials, such as shortest path length, fastest movement, optimal acceleration, minimal jitter, maximum height and other metrics, to provide pairing with improved performance.

The manual interrupt 606 may be adapted to require the therapist after a stimulation from the automatic software to press the manual interrupt 606 to indicate a new stimulation can be permitted. This allows the physician or patient to reset the object 802 or for the physician to demonstrate the movement without accidentally causing a stimulation.

In accordance with another embodiment, EMG (muscle electrical activity) may be measured and used to trigger paired vagus nerve stimulation. It is also possible to quantify or image specific movements of the patient such as a patient's walking gait, eye position or tongue position and pair them with VNS. Muscle activity in muscle groups that are only partly under voluntary control (e.g. bladder and sphincter) may be used to trigger paired vagus nerve stimulation.

The automated system may support such tasks as: Reach and grasp; Reach and grasp (small/large objects) (gross and fine movements, dexterity); Point and/or press objects with finger (accuracy); Insert small objects into wells of different sizes (accuracy); Flip cards or sheets of paper (Circumduction and dexterity); Lift objects from table; Circumduction and bimanual tasks (mainly involving wrist and distal joints); Lock and key (Circumduction); Turning a doorknob (Circumduction); Open and close a pill bottle (bimanual; flexion extension wrist); Pour water from a pitcher to glass (bimanual).

Motion can be detected using a camera or other detection devices. The system may operate by detecting change in color of the object by a camera, breaking an IR beam PIR motion sensor, engaging a force transducer, turning a knob or dial potentiometer, pressing a button, flipping a switch, activating a motion sensor, activating a piezoelectric sensor, ultrasonic sensors for detecting distance, or any other appropriate measure of motion.

The automated system may be designed to do is to determine a "good" trial and only stimulate on a good trial. A good trial may be determined by comparing the history of past movements, running an appropriate algorithm on a clinically relevant parameter(s) and using this determination to trigger stimulation. Good could be defined ahead of time by speed, acceleration, strength, range of motion, like degree of wrist turn, or any other appropriate defining quality.

Similar automated systems are described in U.S. Pat. Nos. 6,155,971 and 7,024,398.

Figure 15:
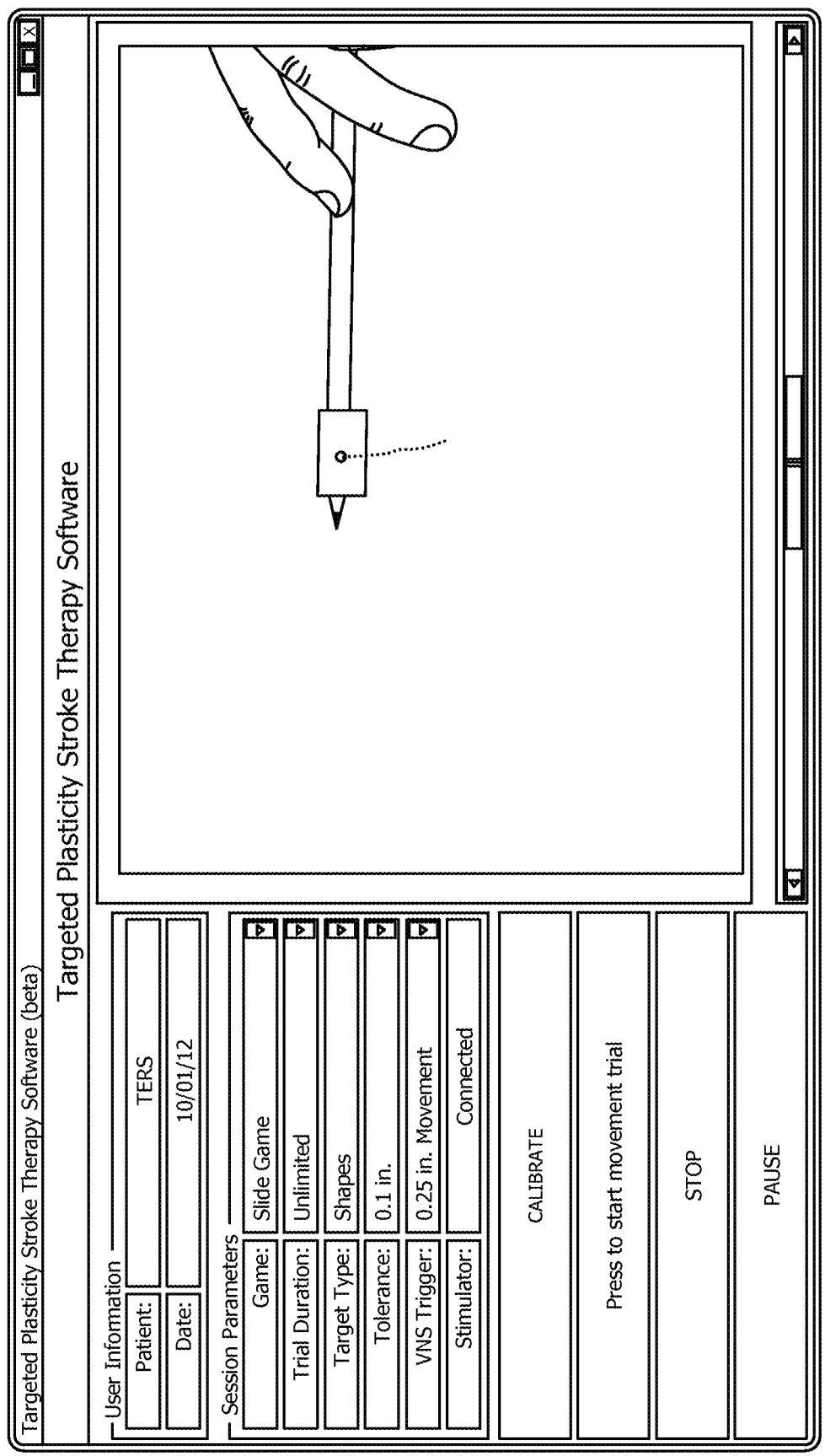
FIG. 15 is a screenshot of an automated therapy screen, in accordance with an embodiment.

With reference to FIG. 15, a screenshot of a specialized automated pairing software is depicted. Patient data and motion parameters may be entered or selected. A camera view detects the motion of an object and provides vagus nerve stimulation, in accordance with the selected parameters.

Support

Although sensory and motor systems support different functions, both systems can exhibit topographic reorganization of the cortex following training or injury. Tone training (conditioning or artificial stimulation) can increase the representation of the tone in the auditory cortex. Operant training on a tactile discrimination task increased somatosensory cortical representation of the digit used in training. Similar changes can occur in the motor cortex following training with precise digit movements. Motivation and frequency of training influence the degree of cortical map plasticity. Deprivation caused by peripheral injury changes the organization of sensory and motor cortices. For example, digit amputation or nerve transection causes receptive fields in the inactivated somatosensory cortex to shift to neighboring digits. Likewise, transecting the facial nerve reduces the number of motor cortex neurons that elicit vibrissae movements while increasing the number eliciting forelimb movements. Targeted lesions to the sensory or motor cortex can cause the surrounding healthy cortical areas to take on some of the damaged area's lost functionality. Drugs that block reorganization of cortical representations in the sensory cortex can also block reorganization in the motor cortex. Collectively, these results suggest that the mechanisms regulating cortical plasticity are common to both sensory and motor cortices.

The vagus nerve may send afferents to a number of nuclei known to release neuromodulators associated with cortical plasticity, including the locus coreleus, raphe nuclei, and the basal forebrain. The vagus nerve has several efferents to major organs in the body, including the heart; however, a large portion of the vagus nerve consists of afferent connections to several targets in the midbrain. Low-current stimulation of the left vagus nerve is a commonly used treatment for drug-resistant epilepsy that is associated with minimal risks. Complications associated with stimulation to the heart are avoided due to the limited contributions of the left vagus nerve to cardiac activity and the minimal levels of current. Unilateral stimulation of the vagus nerve can result in bilateral activation of the nucleus of the solitary tract and its projections to the locus coeruleus and raphe nucleus. Activation of the locus coeruleus can lead to activation of the nucleus basalis through α1 adrenoreceptors. Although the exact mechanisms of action are not entirely yet understood, VNS has demonstrated several beneficial effects for major depression, mood enhancement, improved memory, decision making, and improved cognitive abilities in Alzheimer's patients, and it reduces edema following brain trauma. Due to the known release of multiple neuromodulators, VNS has recently become an object of study in regulating cortical plasticity.

Pairing VNS with motor therapies can be accomplished using several types of pairing systems. A timing control device can initiate or provide the therapy and the VNS at appropriate times. A timing control device can monitor the therapy and provide VNS at appropriate times during the therapy. A timing control device can receive manual inputs from a patient or clinician during the therapy and generate VNS at appropriate times.

Several experiments have been performed that demonstrate the effectiveness of pairing motor therapy with VNS. The methods and results of those experiments are described below.

The wheel spin task required the rat to spin a textured wheel towards themselves. Rats used movements of the wrist and digits to complete this task. Stimulation and reward occurred after the rat spun the wheel about 145° within about one second period. The lever press task required the rat to depress a spring-loaded lever twice within about 0.5 seconds. The range of motion required to complete this task pivoted primarily around the shoulder joint. Stimulation and reward occurred after the second lever press.

Although sensory and motor systems support different functions, both systems exhibit dependent cortical plasticity under similar conditions. If mechanisms regulating cortical plasticity are common to sensory and motor cortices, then methods generating plasticity in sensory cortex should be effective in motor cortex. Repeatedly pairing a tone with a brief period of VNS increases the proportion of primary auditory cortex responding to the paired tone. It was predicted that repeatedly pairing VNS with a specific movement would result in an increased representation of that movement in primary motor cortex. As such, VNS was paired with movements of the distal or proximate forelimb in two groups of rats. After about five days of VNS movement pairing, intracranial microstimulation was used to quantify the organization of primary motor cortex. Larger cortical areas were associated with movements paired with VNS. Rats receiving identical motor training without VNS pairing did not exhibit motor cortex map plasticity. These results suggest that pairing VNS with specific events may act as a general method for increasing cortical representations of those events. VNS-movement pairing could provide a new approach for treating disorders associated with abnormal movement representations.

Repeatedly pairing VNS with a tone may cause a greater representation of that tone in primary auditory cortex. This map expansion is specific to tones presented within a few hundred milliseconds of VNS. No previous study has reported the effects of pairing VNS with a specific movement on cortical plasticity. If the mechanisms regulating map plasticity in the auditory cortex are the same in the motor cortex, then VNS-paired with a movement should generate map plasticity specific to the paired movement. In one embodiment, VNS was paired with a specific movement to test if this method could be used to direct specific and long-lasting plasticity in the motor cortex.

In one embodiment, thirty-three rats were randomly assigned to receive a vagus nerve cuff electrode or a non-functional, sham vagus nerve cuff electrode. After recovery from the surgery implanting the nerve cuff, thirty-one rats were trained to perform one of two operant motor tasks using either their proximal or distal forelimb. After the rats learned to reliably generate the required movement, VNS was paired with the movement several hundred times each day for about five days. For twenty-five of these rats, intracranial microstimulation (ICMS) was used to quantify the reorganization in the primary motor cortex about 24 hours after the last training session. Instead of ICMS, six of the non-stimulated rats received ischemic motor cortex damage and were retested to confirm that accurate performance of the task requires motor cortex. Motor cortex ICMS was performed on two rats that had functional VNS electrodes and received the same amount of VNS but received no motor training. An additional group of eight experimentally naïve rats that had not received motor training or VNS also underwent motor cortex ICMS.

A comparison of the motor maps from the rats with sham cuffs to the rats with functional cuffs allows a determination as to whether pairing VNS with the movements enhances cortical plasticity. Comparison of the motor maps from rats that were performing a task during VNS with rats that were not performing a task during VNS allows a determination as to whether the motor task was required to generate motor cortex plasticity.

Forty-one adult, female Sprague-Dawley rats were used in this experiment. The rats were housed in a 12:12 hour reversed light cycle environment to increase their daytime activity levels. During training, the rats' weights were maintained at or above 85% of their normal body weight by restricting food access to that which they could obtain during training sessions and supplementing with rat chow afterward when necessary.

Rats were implanted with a custom-built cuff electrode prior to training. Stimulating cuff electrodes were constructed as previously described. In one embodiment, two TEFLON-coated multi-stranded platinum iridium wires were coupled to a section of Micro-Renethane tubing. The wires were spaced about two mm apart along the length of the tubing. A region of the wires lining the inside circumference of the tube about eight mm long was stripped of the insulation. A cut was made lengthwise along the tubing to allow the cuff to be wrapped around the nerve and then closed with silk threads. This configuration resulted in the exposed wires being wrapped around the vagus nerve at points separated by about two mm, while the leads exiting the cuff remained insulated. These insulated wires were tunneled subcutaneously to the top of the skull and attached to an external connector. A second group of randomly chosen rats received similar cuffs, but with silk threads in place of the platinum iridium wires.

In one embodiment, all the steps of the surgeries were the same regardless of the type of cuff implanted. Rats were anesthetized using ketamine hydrochloride and xylazine with supplemental doses provided as needed. After rats were no longer responsive to toe pinch, incision sites atop the head and along the left side of the neck were shaved and cleaned with betadine and about 70% isopropyl alcohol. The application of opthomalic ointment to the eyes prevented corneal drying during the procedure and a heating pad maintained the rats' body temperature at about 37° Celsius (C). Doses of cefotaxime sodium and a dextrose/Ringer's solution were given to the rats before and during the surgery to prevent infection and provide nourishment throughout the surgery and recovery. Bupivicaine injected into the scalp and neck further ensured that the rats felt no discomfort during surgical procedures. An initial incision and blunt dissection of the scalp exposed the lambda landmark on the skull. Four to five bone screws were manually drilled into the skull at points close to the lambdoid suture and over the cerebellum. After an acrylic mount holding a two-channel connector was attached to the anchor screws, an incision and blunt dissection in the neck exposed the left cervical branch of the vagus nerve. As in humans, only the left vagus nerve was stimulated because the right vagus nerve contains efferents that stimulate the sinoatrial node and can cause cardiac complication.

In one embodiment, eighteen rats received the platinum iridium bipolar cuff-electrodes while another thirteen received the sham cuffs in which silk thread replaced the platinum iridium wires. Leads (or silk threads) were tunneled subcutaneously and attached to the two-channel connector atop the skull. All incisions were sutured and the exposed two-channel connector encapsulated in acrylic. A topical antibiotic cream was applied to both incision sites. After surgery, the rats with silken threads looked identical to the rats with wired cuffs after the surgeries. Rats were provided with amoxicillin (about 5 mg) and carprofen (about one mg) in tablet form for three days following the surgeries and were given one week of recovery before training began. During the week of recovery, rats were habituated to having the stimulator cable coupled to the two-channel connector on their heads. This method of cuff electrode construction, implantation, and stimulation delivery has repeatedly been shown to consistently result in VNS that persists over the full-term of the experiment.

In one experiment, rats were trained on either the wheel spin task (n=10 rats) or the lever press task (n=21 rats). Training occurred in two daily sessions for five days each week. Both tasks involved quick movement of the forelimb in order to receive a sugar pellet reward. Rats initiated each trial, but a delay of at least two seconds was required between trials to allow the rats to eat the sugar pellet. The wheel spin task required the use of muscles located primarily in the distal forelimb, especially the wrist, while the lever press task required the use of the shoulder and the proximal forelimb.

The initial shaping procedures were similar for both motor tasks. In one embodiment, rats were placed in a cage and allowed to freely explore the area. A tether was coupled to the rats' heads to familiarize the animals with the feeling of the connection. Each time the rats approached the response device (e.g., the lever or wheel), they received a 45 mg sugar pellet dispensed into a pellet dish located within the cage. Restrictions were gradually placed on rewarding the rats' proximity to the response device until the rats had to be next to, and then touching, and finally using the device to receive the reward. An experimenter conducted shaping procedures manually. Rats typically took four 30-minute sessions to become familiarized to the response device. After shaping, all training sessions were automated using custom-written programs.

In one embodiment, rats that trained on the wheel spin task were required to spin a textured wheel below the floor of the training cage to receive a sugar pellet reward. Trials were initiated by the rats, but rewards were spaced at least two seconds apart by the computer program. In one embodiment, rats were initially rewarded for spinning the wheel about 3° within a one-second period when each new stage began. After about 35 successful spins of the wheel, the degree of rotation required for a reward increased to about 30°, then about 75°, and finally about 145°. After about 35 rewards at the highest rotational requirement, the rats advanced to the next stage of training (e.g., more restricted access to the wheel) where they repeated all of the levels of increasing rotation again as previously described. Rats demonstrated a paw preference early in training and continued to use that paw for the remainder of the sessions.

In one embodiment, rats depressed a lever initially located inside the training cage to receive a sugar pellet reward. The training cage was a wire cage with dimensions of approximately 20 centimeter (cm)×20 cm×20 cm with a Plexiglas wall opposite the door. In one embodiment, all training sessions other than the shaping sessions were about fifteen minutes long and occurred about twice daily. Trials were initiated by the rats, but rewards were only given to trials occurring at least five seconds apart. After receiving about 60 pellets in about two shaping sessions by pressing the lever, the rats learned to press the lever twice in an about three-second period for the same reward. The interval between lever presses that elicited a reward was reduced from about three seconds to about two seconds, then about one second, and finally about 500 milliseconds (ms), with about 15 successful trials as the criterion for advancing. After successfully pressing the lever twice within about 500 ms about forty-five times, the lever was gradually withdrawn out of the cage. The lever was initially located about four cm inside the cage, then moved to about two cm inside the cage, and then to about 0.5 cm, about 1.5 cm, and about 2.0 cm outside of the cage. The criterion for retracting the lever was about 15 successful double-lever presses for each position, except for about 0.5 cm outside the cage, which required 30 successful trials. In one embodiment, rats reached through a window in the Plexiglas wall that was about one cm×about seven cm to reach the lever outside the cage. The edge of the window was located about two cm from the cage wall, while the lever was offset so that the middle of the lever lined up with the edge of the window furthest from the wall. This arrangement restricted the rats so that they could only comfortably press the lever with their right paw. This aspect of the task design was important for confirming the importance of the motor cortex for the lever press task with motor cortex lesions.

To confirm that accurate performance on the lever press task requires motor cortex, six rats implanted with the nerve cuffs and trained on the lever-press task without stimulation received motor cortex lesions and were retested for about two days following about one week of recovery. Based on procedures by Fang et al., (2010), the vasoconstrictor endothelin-1 was used to selectively lesion the caudal forelimb area of the motor cortex. Basic surgical procedures for cleaning, anesthesia, and post-surgical care were the same as the cuff implantation surgery. After cleaning the top of the head, an incision was made longitudinally and a craniotomy was performed over the primary motor cortex caudal forelimb area contralateral to the trained forelimb (about 2.75 mm to about −0.75 mm anteroposterior and about 2.25 mm to about 3.75 mm mediolateral, relative to bregma). Endothelin-1 (about 0.33 microliters (μL) of about 0.3 micrograms (μg) mixed in about 0.1 μL saline) was injected at a depth of about 1.8 mm using a tapered Hamilton syringe along a grid within the craniotomy at about 2.5 mm, about 1.5 mm, about 0.5 mm, and about −0.5 mm anteroposteriorally, and about 2.5 mm and about 3.5 mm mediolaterally relative to bregma for a total of eight sites according to one embodiment. KwikCast silicone gel was used to replace the removed skullcap and the skin was sutured. The lever press task was the only task tested with motor cortex lesions due to the ease with which the forelimb used in the task could be restricted. The lever press task could not be completed with the left forelimb because of the cage design. Lesions were made in the left motor cortex forcing the rat to try to use its impaired right forelimb to complete the task. Impairments to the distal forelimb accompany impairments to the proximal following motor system lesions. Additionally, the lesion size covers the entire caudal forelimb area; therefore, it is expected that impairments to the lever press task would also indicate impairments to the wheel spin task.

During the final stage of the motor tasks, reaching through a window about 1.2 cm wide and spinning the wheel about 145° within about one second period or pressing the lever located about two cm outside the cage twice within about 500 ms triggered a food reward and VNS. Stimulations were delivered approximately 75 ms after the wheel reached 145° or the lever triggered the second press. Rats typically continued to spin the wheel or press the lever beyond the required criterion, such that the movements were still occurring during VNS. In one embodiment, VNS was always delivered as a train of about 15 pulses at about 30 hertz (Hz). Each about 0.8 milliamps (mA) biphasic pulse was about 100 microseconds (μs) in duration. The train of pulses was about 500 ms in duration. Previous studies have demonstrated that the amplitude of electroencephalographic measures may be reduced and neuronal desynchrony may increase during VNS using the described electrode implantation, which may indicate a successful stimulation of the vagus nerve. VNS-movement pairing during the final stage of training continued for one week (in one embodiment, 10× about 30 minute sessions for the wheel-spin task and 10× about 15 minute sessions for the lever-press task), delivering around 1,200 total stimulations. Previous research has shown that this form of VNS does not alter heart rate, blood oxygenation level, or ongoing behavior, suggesting that the stimulation is neither aversive nor rewarding to the animals.

In one embodiment, connections and stimulations from the external stimulator to the rats were identical between rats implanted with functional or sham VNS electrode cuffs. The sham cuffs with silk threads in place of platinum iridium leads did not carry an electrical charge when stimulated. This difference in the cuffs allows experimenters to remain blind during training to stimulated and sham rats.

The day after the last training session of VNS movement pairing, the organization of primary motor cortex contralateral to the trained paw was defined using standard ICMS mapping procedures. In one embodiment, an additional eight rats that did not train or receive VNS also underwent ICMS procedures to the left cortex to compare the effects of training on motor cortex organization. After placing the rat in a stereotaxic frame with a digital readout, a craniotomy was performed to expose the motor cortex. In one embodiment, parylene-coated tungsten electrodes were inserted to a depth of about 1,800 micrometers. Stimulation occurred following a grid with about 500 μm spacing. Sequential electrode placements were made at least one mm apart where possible. ICMS was delivered once per second. In one embodiment, each stimulation consisted of an about 40 ms pulse train of about ten 200 μs monophasic cathodal pulses delivered at about 286 Hz. Stimulation intensity was gradually increased (from about 20 to about 200 microamperes (μA)) until a movement was observed. If no movement was observed at the maximal stimulation, then the site was deemed nonresponsive. The borders of primary motor cortex were defined based on unresponsive sites and stopped at the posterior-lateral vibrissae area, which is known to overlap the somatosensory cortex.

In one embodiment, motor mapping procedures were conducted with two experimenters, both blind to the experimental condition of the rat. The first experimenter placed the electrode and recorded the data for each site. Because the motor cortex is organized with similar movements often occurring in the general vicinity of each other, the second experimenter was kept blind to the electrode placement to avoid potential biasing. The second experimenter delivered stimulations while observing which parts of the body moved in response. Movements were classified based on the part of the body that moved using the threshold stimulation current. Larger movements were obtained using higher current stimulations and were used when necessary to disambiguate movements too small to confidently classify at threshold levels. The first stimulation site was placed in an area often resulting in movement of the lower forelimb. Subsequent stimulation sites were randomly chosen and did not extend beyond established border (e.g., unresponsive) sites. Movements of the vibrissae, face, eye, and neck were classified as "head". Movements of the shoulder, elbow, and upper forelimb, e.g., proximal forelimb, were classified as "upper forelimb". Movements of the wrist and digits were called "distal forelimb". "Hindlimb" included any movement in the hindlimb of the rat. Cortical area was calculated by multiplying the number of sites eliciting a response by about 0.25 $mm^2$. Four sites equal about one $mm^2$.

To confirm that VNS alone does not produce motor cortex map reorganization, two rats that were never trained to perform a motor task were placed into a training cage and received randomly delivered VNS (e.g., not paired to a specific movement). Except for the movement pairing, VNS in this group was identical to the groups above. In one embodiment, each animal was passively stimulated for two 30-minute sessions per day with an about two-hour break between sessions, and repeated for about five days. Within each session, stimulation occurred for a time from about 8 to about 16 seconds, giving an average stimulation time of about 11.25 seconds. At the end of each session, about 160 stimulations were given, which amounted to about 1,600 stimulations. Animals were ICMS mapped about 24 hours following the final passive VNS session.

Rats were shaped to the wheel spin task in about 4±0.3 sessions and the lever press task in about 4±0.3 sessions. Rats reached the last stage of the wheel spin task in about 27±5 sessions and the lever press task in about 8±1 session. The percent of successfully completed trials on the wheel spin task on the first day of VNS paired training was about 77±4%. The same measure for the lever press task on the first day of VNS paired training was about 78±4%. Microelectrode mapping techniques were used to determine the organization of the motor cortex after five days of VNS paired training on the last stage. Maps of the motor cortex were derived from about 3,595 electrode penetrations (average about 103 sites per animal).

In all rats tested, the anterior portion of the motor map generated movements of the rat's head, including the jaw, vibrissa, and neck. The middle region of the map generated movements of the forelimb and the posterior region generated movements of the hindlimb. As in earlier reports, it was possible to divide the forelimb area into a small rostral region that is mostly surrounded by head responses and a larger caudal forelimb area that borders the hindlimb area.

In one embodiment, the organization of primary motor cortex was not significantly altered by training without VNS. The average area representing the distal forelimb, proximal forelimb, head, and hindlimb were not significantly different across the naïve, wheel spin, or lever press trained rats that had sham VNS cuffs electrodes and received no VNS. As a result, these three control groups are averaged for group analyses and referred to as the non-VNS group.

In one embodiment, rats that received VNS paired with the wheel spin task exhibited a significant reorganization of the motor cortex. In the non-VNS rats, the head and distal forelimb occupy approximately the same amount of cortical area Hindlimb and proximal forelimb comprises a smaller region of the motor map. Wheel spin/VNS pairing resulted in an about 15% larger distal forelimb area (about 1.0 $mm^2$), an about 25% smaller head area (about −1.75 $mm^2$), and no proximal forelimb area in this particular animal compared to the naive. These changes in cortical area for the Wheel spin/VNS paired group were pronounced when compared to the non-VNS group. On average, pairing VNS with the wheel spin task resulted in an about 32% increase in the cortical area representing the distal forelimb compared to the non-VNS group. This increase was accompanied by an about 38% smaller head area and an about 63% smaller proximal forelimb area, but no change in the area devoted to hindlimb. These results suggest that repeatedly pairing VNS with a particular movement can generate a specific increase in the motor cortex representation of that movement.

To confirm that the observed cortical plasticity was specific to the movement paired with VNS, the reorganization of motor cortex was documented in rats that received VNS paired with a lever press task. Since this task primarily involves movement of the proximal forelimb, an increased proximal forelimb representation after lever press/VNS pairing was expected. The lever press/VNS rat had about 1600% (about four $mm^2$) more area devoted to the proximal forelimb area compared to the naïve rat. Pairing VNS with the lever press movement reduced the head area by about 39% (about −2.75 $mm^2$) and distal forelimb area by about 59% (about −4 $mm^2$) in this rat compared to the naïve rat. Like the wheel spin/VNS trained rat, the lever press/VNS rat had the same sized hindlimb representation as the naïve rat. These examples suggest that the motor cortex plasticity observed following VNS-movement pairing may be specific to the paired movement and not a general effect of VNS.

On average, rats that received VNS during the lever task exhibited about 159% increase in the proximal forelimb area compared to the non-VNS group. The lever press/VNS group had an about 23% smaller distal forelimb area and an about 29% smaller head area than the non-VNS group. The most profound differences were observed between the wheel spin/VNS rats and the lever press/VNS rats. Although both groups received identical VNS, wheel spin trained rats had an about 72% larger distal forelimb area than the lever press rats and the lever press rats had an about 598% larger proximal forelimb area compared to the wheel spin trained rats. These results may demonstrate that VNS-movement pairing can generate large-scale reorganization of motor cortex and confirm that the reorganization is specific to the movement repeatedly paired with VNS.

In one embodiment, VNS was delivered at random times in two rats before documenting the organization of motor cortex using ICMS techniques. Motor cortex in these rats was similar to naïve rats and there was no evidence of the reorganizations that were observed after either the lever press or the wheel spin movements were paired with VNS. This observation combined with task specificity of the motor cortex plasticity observed in the trained rats that received VNS suggests that VNS-movement pairing may be sufficient to generate motor cortex reorganization.

In one embodiment, there was no difference in the average stimulation thresholds for the groups receiving movement paired VNS and the non-VNS group. The differences in average stimulation thresholds between past studies and the current study may be due to our using a somewhat deeper level of anesthesia. The rats trained with VNS paired on the wheel spin task had an average distal forelimb stimulation threshold not too different from the wheel spin trained group with sham VNS cuff electrodes. The VNS paired with lever press group's proximal upper forelimb stimulation thresholds was not considerably different from the lever press group trained with sham VNS cuff electrodes. Similar stimulation thresholds between paired-VNS and non-VNS trained rats demonstrate that the observed movement representation reorganizations are not due to altered levels of excitability in the cortex. This result is consistent with several papers that have found cortical representation changes in the motor cortex from training occurs without ICMS threshold changes. Morphological changes, such as synaptogenesis, have been observed with past motor cortical reorganization accompanying training and may account for a mechanism of change in movement paired VNS.

The performance on the lever press task before and after ischemic motor cortex damage in six rats was compared. In one embodiment, performance was markedly impaired in every rat. Average performance fell from 93±1% successful double-tap attempts for the last two days before surgery to 75±5% for the two days of testing conducted after a week of recovery. This result tends to confirm that this task like other skilled motor tasks may depend on motor cortex for accurate performance.

The task performance in each group was compared to confirm that movement paired VNS does not make the task more difficult. In one embodiment, no behavioral differences were observed between VNS and sham groups on the wheel spin task in the total number of successful trial, the velocity at which the wheel was spun, or the percentage of successfully completed trials per session. VNS rats showed no impairment on the lever press task and, in fact, exhibited shorter lever press intervals and triple pressed the lever more often than the sham rats. Although VNS enhanced some aspects of the lever press task, the percent of successful trials and the total number of successful trials were not different between the VNS and sham rats. These results may indicate that VNS is unlikely to have enhanced map reorganization by making the task more difficult.

It was predicted that repeatedly pairing brief stimulation of the vagus nerve with a specific movement would result in a larger representation of that movement in the motor cortex. As such, about 0.5 sec of VNS was delivered each time rats used their distal forelimb to rotate a wheel. After several hundred pairings, the cortical representation of the distal forelimb was markedly larger in these rats compared to naïve rats and rats that performed the same movements without VNS. A second group of rats was trained on a motor task using a different part of their body to confirm that map reorganization was specific to the movement paired with VNS. Pairing VNS with a lever press task that required the use of the proximal forelimb resulted in a markedly larger proximal. Impaired performance in a group of rats following ischemic lesions to the caudal forelimb area tends to confirm the involvement of the motor cortex in this task. The observations that map expansion was specific to the movement paired with VNS and that neither of the tasks without VNS nor VNS without the task training generated map reorganization indicates that movement paired VNS is sufficient to direct map plasticity.

Pairing VNS with a motor event generated cortical plasticity comparable to that observed using a similar paradigm in the auditory system. Presenting a tone with a brief period of VNS causes a significant expansion of the paired tone's representation in the auditory cortex. Presenting tones or VNS alone did not alter the auditory cortex's tonotopic organization. These two studies suggest that the plasticity enhancing mechanisms of event-paired VNS may be shared with the auditory and motor cortex.

A number of studies have reported that training on skilled motor tasks increases cortical representations for the movements involved. The results disclosed herein do not contradict these findings, as one of the landmark studies demonstrating training induced cortical plasticity using a skilled reaching task also demonstrated a lack of reorganization for a lever press task. The lack of observed cortical change following training on the lever press and wheel spin tasks may be due to a number of reasons. The cortical reorganization observed in a skilled reaching task has been attributed to the accuracy of the movements necessary to complete the task which may be absent in our lever press and wheel spin tasks. There is also a possibility that the sampling distance of about 500 μm is too coarse to see cortical changes associated with tasks in the current study, although this spacing has previously demonstrated training induced plasticity in the aforementioned skilled reaching task. Another possibility is the cortical changes observed following motor and auditory learning have been shown to be transient while the acquired skill remains stable over time. The lever press and wheel spin trained rats were mapped approximately 10 and 20 days after their initial training session, respectively, possibly occurring after cortical changes associated with training would have been observed. If this possibility occurred, then the VNS-paired training may have prolonged or reestablished the observed changes in the motor cortex organization.

The exact mechanisms by which VNS directs plasticity in motor or sensory cortex are unknown. VNS causes the release of several molecules known to enhance cortical plasticity, including acetylcholine, norepinephrine, serotonin, and brain derived neurotrophic factor. Perfusing norepinephrine into an adult cat's visual cortex produces kitten-like plasticity in a test of ocular dominance shifts following monocular deprivation. Serotonin specific neurotoxins and receptor blockers prevent normal ocular dominance shifts in kittens in monocular deprivation, implicating the importance of serotonin for normal plasticity. Another important study showed that enhancing serotonin release with fluoxetine can stimulate plasticity in adult cats. Blocking the release of acetylcholine prevents cortical plasticity and interferes with skill learning and recovery from brain damage. The use of the muscarinic antagonist scopolamine blocks the effect of VNS on spontaneous firing rate in the auditory cortex, further supporting the influence of VNS on the cholinergic system. Adding brain derived neurotrophic factor induces plastic changes in ocular dominance shifts in adult rats following monocular deprivation. Combining more than one of these elements can lead to greater plasticity than the influence of the elements singularly. The ability of VNS paired with wheel-spin or lever-press training to produce cortical plasticity supports the importance of the VNS triggered release of these molecules in enhancing cortical plasticity. VNS is likely to generate cortical map plasticity specific to the associated event through the synergistic action of multiple plasticity enhancing molecules.

The simultaneous presentation of VNS with a specific sensory or motor event can be sufficient to increase cortical representation of that movement. As discussed above, a sugar pellet was used to reward the animal's behavior immediately after the completion of a trial. As a result, VNS was delivered during the behavioral task that finished just a few seconds prior to the animal eating the pellets. It would not have been surprising to see an increased representation of the head and jaw in this study.

In a previous study, our lab demonstrated that changes in auditory cortex were temporally specific to tones paired with VNS. Two randomly interleaved tones were presented every about 15 to about 45 seconds for several thousand trials to a rat with only one of the tones paired with VNS. The number of sites responding to the VNS paired tone increased significantly, while the number of sites for the tone presented within tens of seconds of the VNS did not. These observations are consistent with past studies demonstrating that pairing nucleus basalis stimulations with tones only alters the tone's representations when stimulations occurred within seconds of the tone presentation.

The results disclosed herein demonstrate that the head representations did not increase because of VNS just prior to chewing. This result indicates that the plasticity enhancing actions of VNS are temporally precise, lasting less than about one or about two seconds. These results demonstrate that brief pulses of VNS can be used to direct highly specific plasticity. Additionally, VNS without paired behavioral training did not result in map reorganization, further supporting our conclusion that the cortical changes triggered by VNS are enhanced by task specific pairing. Methods for enhancing plasticity that rely on slow-acting mechanisms may not be as effective in generating the same accuracy of plasticity as VNS-pairing. Pharmaceuticals often elevate or diminish certain neurotransmitters for several hours. Several movements or sensory events may occur repeatedly during this time, potentially creating unwanted plasticity. The temporal precision of the VNS-pairing method for enhancing cortical plasticity should offer advantages in efficiency and efficacy as compared to methods with less precise actions.

In one embodiment, motor map expansions did not accompany enhanced task performance in rats trained on the VNS paired wheel spin or lever press tasks. This is not necessarily at odds with the prediction that event paired VNS increase functional recovery through increasing functional plasticity following cortical damage. Map reorganization has been shown to be important for enhancing behavioral outcomes during the learning process (Reed et al., 2011). Rats demonstrating increased tonotopic representations for low frequencies following paired nucleus basalis stimulation demonstrated faster learning of a tone discrimination task compared to controls. However, rats that had already learned the tone discrimination did not behaviorally benefit from the induced plasticity. From these results, the authors concluded that "cortical map expansion plays a major role in perceptual learning but is not required to maintain perceptual improvements". In the present disclosure, the rats had already learned the tasks when they began receiving VNS, otherwise they may have demonstrated an accelerated learning rate compared to the sham groups. The enhanced propensity for cortical reorganization accompanying event-paired VNS may increase rehabilitative learning.

Stroke and traumatic brain injury often damage movement-controlling areas of the motor cortex resulting in hemiparesis or hemiplegia. Following cortical injury, lost motor representations can partially regenerate in neighboring areas within motor cortex. The size of the regenerated representations is highly correlated with the functional recovery of lost movements, but this recovered area and ability is a fraction of those seen pre-injury. Physical training in healthy animals can greatly increase cortical representation of the muscles used, during learning of the task, but rehabilitative physical training in rats after a motor cortical injury is less effective at generating this increased representation. Movement paired VNS in intact rats generates a comparable amount of cortical plasticity in approximately the same amount of time as physical training. Movement paired VNS is also able to enhance plasticity where plasticity is not observed with training alone. Since increased cortical plasticity is related to increased functional recovery following cortical injury, it is possible that movement paired VNS could enhance the recovery of specific motor functions following cortical injury, compared to rehabilitative training alone.

Non-invasive brain stimulation techniques, such as repeated transcranial magnetic stimulation and transcranial direct current stimulation, show promise as methods for inducing better functional recovery with rehabilitative training following stroke than training alone. These techniques apply a localized current to the scalp to manipulate electrical fields in the cortex without the need for surgery or pharmaceuticals. These methods are thought to work primarily through influencing levels of cortical excitability, but also cause increased levels of neurotrophic factors, serotonin, and dopamine. Combining paired-VNS methods with non-invasive brain stimulation may lead to even greater recovery than either method used alone through activating different plasticity enhancing mechanisms.

Periodic VNS is Food and Drug Administration (FDA) approved as a safe and effective treatment of certain types of refractory epilepsy as well as treatment-resistant depression. Protocols for treating epilepsy comprise about 30 seconds of VNS every about five minutes, 24 hours per day. Periodic VNS using a stimulation protocol similar to that used in treating epilepsy has improved functional recovery in rats with fluid percussion injury to the cortex. This protocol requires about 145 times the daily current injection compared to what was used in the method disclosed herein. The above-disclosed results tend to demonstrate that motor and auditory events can be precisely timed with VNS to markedly alter motor and auditory system organization, respectively. It seems likely that therapies using paired VNS might be a more effective therapy for increasing functional recovery following cortical damage.

Selectively pairing VNS has already shown promise in normalizing abnormal cortical organizations in the treatment of tinnitus in rats. The overrepresentation of a tone was reduced by pairing VNS with tones spanning the rats hearing range except for the tones near the tinnitus frequency. This eliminated the behavioral correlate of tinnitus in rats for several months past the cessation of the treatment. A similar strategy of pairing VNS with movements may improve the treatment of disorders related to abnormal representations in the motor system, such as dystonias. Although the causes are not fully understood, patients with dystonia demonstrate disturbed cortical inhibition that is improved with the application of transcranial magnetic stimulation. Current evidence supports that reducing the overrepresented motor area during these treatments is associated with a reduction in dystonic symptoms. As disclosed herein, the larger representations observed from the VNS paired movements were accompanied by smaller nearby cortical representations, such as movements of the head. Selectively increasing the size of surrounding muscle representations might decrease the overrepresentation of the dystonic muscles. Movement paired VNS of non-dystonic, surrounding movements may decrease the overrepresentation of the dystonic muscles. The strategic pairing of non-dystonic movements with VNS provides a novel potential therapy to treat focal dystonia.

Clinical and pre-clinical data has been collected to support the effectiveness of the tinnitus therapy and parameters.

Selection of the vagus nerve for stimulation is not arbitrary. The vagus nerve produces specific effects when stimulated at a specific time relative to a physical task. The peripheral nervous system, central nervous system including the brain and spinal cord are typically used by others as therapeutic stimulation locations. The choice of stimulation location largely determines the behavioral and neurophysiologic outcome. Even though similar neural populations are activated by input from two different locations, the manner in which they are activated, for example, the pattern of activity generated within the neuron population may depend on the time course of activation, release of one or more neuromodulators, attention state, etc. The neurophysiological consequences therefore are bound to be different. Given the large (and unknown) number of variables that can influence the activation of a given neural population, the mechanisms are likely to be complex and unpredictable. There is no calculus to determine which locations may produce which effects. Finding a location that produces a given effect can only be done experimentally. It is not valid to suggest that stimulation at one location makes it obvious to stimulate at a different location, even if the goal is to stimulate the same population of neurons.

The same can be said for stimulation parameters. At a given stimulation location, stimulation according to one set of parameters may not necessarily produce the same (or similar) effects as a stimulation according to another set of parameters. The frequency of stimulation, the current amplitude of stimulation, the duration of each stimulation, the waveform of stimulation, as well as other stimulation parameters can change the results of stimulation.

Our experiments have shown that the effect generated by VNS pairing is very short, less than 15 seconds. A first tone at a first frequency when paired with VNS generated an increase in the number of neurons that respond to the paired frequency. A second unpaired tone at a second frequency, played 15 seconds after the paired VNS did not show a corresponding increase in the number of neurons that respond to the second frequency. Nothing in the prior art indicates this kind of precise timing requirement.

Similarly, we have performed experiments in which multiple tones at a given frequency were paired with VNS and given 30 seconds apart. This was done in the tinnitus study (Engineer et al., 2011) in which VNS was paired with each of the randomly interleaved tones every 30 seconds (e.g., 1.3 kilohertz (kHz)+VNS, then wait for 30 seconds, then give 6.3 kHz+VNS, and then wait for 30 seconds and so on). The tones were selected such that they surrounded the tinnitus frequency and the tinnitus frequency itself was excluded. The idea was to shrink the representation of the tinnitus frequency thereby restoring the map and synchronous activity back to normal. When the same tones were presented eight seconds apart, the effect was less than if the tones were presented 30 seconds apart, which was surprising.

To cite another example, we have performed a series of experiments where a tone is repeatedly paired with a foot-shock to establish a conditioned fear response. Subsequently, when the tone was presented without a foot-shock, the rat would freeze, anticipating a foot shock. If the tone, without the foot-shock, is then presented repeatedly, the fear caused by the tone would eventually be extinguished, undoing the conditioning. By pairing the tone (without the foot-shock) with VNS, the fear is extinguished much more quickly. However, presenting the tone by itself and then giving VNS minutes later, the fear is extinguished at the normal rate.

Further experiments have demonstrated the effect of the described therapy. VNS paired with a movement improves motor performance in a rat model of ischemic stroke. VNS paired with movement improves a motor deficit several weeks after an ischemic lesion. VNS delivered two hours after rehabilitation did not show any significant difference from rehabilitation alone.

These results demonstrate that the precise timing between VNS and the event as well as the interval separating the VNS-event pairings appear to be important for inducing highly specific plasticity.

Neurostimulation does not behave in a predictable fashion. Different stimulation locations produce different results, even when both locations are cranial nerves. For example, synchronization in the cerebral cortex is a manifestation of epilepsy. Stimulating the vagus nerve causes desynchronization of the cortex neurons, which has been proposed as a potential mechanism for how vagus stimulation prevents an epileptic seizure. Stimulation of the trigeminal nerve, another cranial nerve, causes desynchronization as well. To determine whether the plasticity induced by VNS is specific to the vagus nerve, we paired stimulation of the trigeminal nerve with a 19 kHz tone. However, when we paired trigeminal stimulation with a tone, in the same way we paired VNS with a tone, we did not observe any plasticity that was specific to the paired tone. Pairing the trigeminal stimulation with a tone at a given frequency did not change the response to that frequency even though it caused desynchronization like in the previous study. Each stimulation location is unique across the full range of effects. It appears that VNS may be uniquely suited to direct cortical plasticity and suggests that the vagus nerve is likely a key conduit by which the autonomic nervous system informs the central nervous system of important stimuli.

Both VNS pairing and nucleus basalis stimulation (NBS) pairing have been shown to change the number of neurons responding to a paired frequency. To be effective, the current amplitude parameter of the stimulation for VNS pairing is more than twice the current amplitude used for NBS pairing. There is an important difference between the neuromodulators released by NBS from those released by VNS, so significant differences between the results of NBS and VNS are expected.

Another experiment demonstrated that pairing a single tone at a specified frequency with VNS increased the number of neurons responding not only to that frequency but to close frequencies, e.g., increased the bandwidth compared to control rats. For NBS pairing, the bandwidth was not significantly different from control rats. Unlike VNS pairing, NBS pairing is highly invasive and may be unsuitable to provide a practical therapeutic benefit. Similar results in one circumstance cannot be extended to predict similar results in another, even slightly different, circumstance. Different stimulation parameters have to be used for effective VNS pairing and NBS pairing.

Because of the specific neurotransmitter mechanisms that generate the specific plasticity required for the described therapies, some drugs may reduce the effectiveness. Muscarinic antagonists, norepinephrine blockers that are centrally acting, norepinephrine uptake inhibitors, nicotinic antagonists, Selective serotonin reuptake inhibitors, drugs that block serotonin and drugs that block dopamine may all reduce the effectiveness of the paired VNS therapies.

None of the description in the present application should be read as implying that any particular element, step, or function is an essential element that must be included in the claim scope: the scope of patented subject matter is defined only by the allowed claims. Moreover, none of these claims is intended to invoke paragraph six of 35 U.S.C. section 112 unless the exact words "means for" are followed by a participle. The claims as filed are intended to be as comprehensive as possible, and no subject matter is intentionally relinquished, dedicated, or abandoned.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 5, 4, etc.; greater than 0.10 includes 0.11, 0.12, 0.15, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 5 percent, 4 percent, 5 percent, . . . , 50 percent, 51 percent, 52 percent, . . . , 75 percent, 76 percent, 77 percent, 78 percent, 77 percent, or 100 percent. Moreover, any numerical range defined by two R numbers as defined in the above is also specifically disclosed. Use of the term "about" means ±10% of the subsequent number, unless otherwise stated herein. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural, or other details supplementary to the disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A motor-deficit-therapeutic method for treatment of a patient who has hemiparesis, the method comprising:
   providing, to the patient afflicted with a hemiparesis, a neurostimulator configured to stimulate a vagus nerve of the patient using electrical, magnetic, optical, acoustic or mechanical stimulation; and
   initiating stimulation of the vagus nerve by the neurostimulator so that at least a portion of the stimulation occurs at least during performance by the patient of a motor therapy session which is hemiparesis-therapeutic, thereby improving the patient's hemiparesis.

2. The method of claim 1, wherein:
   the neurostimulator is further configured to provide a series of electrical pulse trains; or
   the neurostimulator is further configured to provide a programmed sequence of electrical pulse trains.

3. The method of claim 1, wherein:
   the neurostimulator is further configured to provide an electrical pulse train in response to a received signal.

4. The method of claim 1, wherein:
   the motor therapy session includes one or more tasks;
   during the motor therapy session, at least one of the one or more tasks undergoes one or more repetitions;
   at least one task includes one or more associated voluntary muscle movements; and
   two or more sessions comprise a treatment plan.

5. The method of claim 4, wherein:
   a timing of the stimulation is based on completion of one of the one or more repetitions.

6. The method of claim 4, wherein:
   for at least one of the one or more tasks which undergoes one or more repetitions, there are substantially no task-associated voluntary muscle movements during an interval between a given one of the associated one or more voluntary muscle movements and a subsequent one of the associated one or more voluntary muscle movements, the interval having a duration, T, which is greater than zero, T>0.

7. The method of claim 4, wherein:
   the motor therapy session is motor-deficit-therapeutic; and performance by the patient of the one or more voluntary muscle movements includes one or more of:
  moving one or more extremities of the patient based on the associated task;
  reaching at least one hand of the patient towards a targeted object;
  touching a targeted object;
  grasping the targeted object with at least one hand of the patient; or
  moving the targeted object while the targeted object is being grasped with at least one hand of the patient.

8. The method of claim 4, wherein:
each session includes about 3 to about 5 tasks;
in each session, each of the tasks undergoes about 30 to about 75 repetitions; and
a duration of each session is in a range of about 30 minutes to about 120 minutes.

9. The method of claim 4, wherein:
for at least one of the one or more tasks, performance by the patient of the one or more associated voluntary muscle movements includes:
  a planning stage which precedes a corresponding one of the one or more associated voluntary muscle movements.

10. The method of claim 1, wherein:
the stimulation of the vagus nerve does not directly stimulate motor cortex neurons.

11. The method of claim 1, wherein:
the stimulation of the vagus nerve triggers a corresponding release of neuromodulators in motor cortex of the patient during performance by the patient of the motor therapy session.

12. The method of claim 11, wherein:
neuromodulators in the corresponding release of neuromodulators in motor cortex of the patient include acetylcholine and norepinephrine.

13. The method of claim 1, wherein:
current comprising the electrical stimulation of the patient's vagus nerve has an amplitude of no less than about 0.8 milliamperes.

14. The method of claim 1, wherein:
the stimulation is electrical stimulation.

15. The method of claim 1, wherein:
the hemiparesis is improved by improving a motor function of the patient.

16. The method of claim 1, wherein:
the hemiparesis is improved by lessening a motor deficit of the patient.

17. The method of claim 1, wherein:
a timing of the stimulation is based on a successful aspect of one or more voluntary muscle movements by the patient.

18. A method for treatment of a patient who has hemiparesis, the method comprising:
for each of one or more tasks that are intended to be performed, instructing the patient to perform the corresponding task at least once, the corresponding task including one or more associated voluntary muscle movements, and the corresponding task being rehabilitative for hemiparesis; and
during at least partial overlap of at least one of the one or more tasks,
  stimulating a vagus nerve of the patient using electrical, magnetic, optical, acoustic or mechanical stimulation thereby improving the patient's hemiparesis.

19. The method of claim 18, wherein:
the stimulating of the vagus nerve resulting in raised levels of corresponding neuromodulators in motor cortex of the patient, the raised levels of the corresponding neuromodulators creating an opportunity of enhanced hemiparesis rehabilitation for a corresponding period (opportunity period); and
the at least partial overlap pairs the at least one of the one or more tasks and the opportunity period thereby improving the patient's hemiparesis.

20. The method of claim 19, wherein:
the neuromodulators include acetylcholine and norepinephrine.

21. The method of claim 18, wherein:
the vagus nerve is a driver of an ascending neuromodulatory system.

22. The method of claim 18, wherein:
the stimulating of the vagus nerve does not directly stimulate motor cortex neurons.

23. The method of claim 18, wherein, for at least one of the one or more tasks, performance by the patient of the one or more associated voluntary muscle movements includes one or more of:
  moving one or more extremities of the patient based on a current task to be performed;
  reaching at least one hand of the patient towards a targeted object;
  touching a targeted object;
  grasping the targeted object with at least one hand of the patient; or
  moving the targeted object while the targeted object is being grasped with at least one hand of the patient.

24. The method of claim 18, wherein:
performance at least once of each the one or more tasks comprises a session; and
two or more sessions comprise a treatment plan (TP).

25. The method of claim 24, wherein:
during the session, at least one of the one or more tasks undergoes one or more repetitions;
at least one task includes one or more associated voluntary muscle movements; and
a timing of the stimulation is based on completion of one of the one or more repetitions.

26. The method of claim 24, wherein:
each session includes about 3 to about 5 tasks;
in each session, each of the tasks undergoes about 30 to about 75 repetitions; and
a duration of each session is in a range of about 30 minutes to about 120 minutes.

27. The method of claim 18, wherein:
for at least one of the one or more tasks, there are substantially no task-associated voluntary muscle movements during an interval between a given one of the one or more associated voluntary muscle movements that comprise the corresponding task and a subsequent one of the one or more associated voluntary muscle movements that comprise the corresponding task, the interval having a duration, T, which is greater than zero, T>0.

28. The method of claim 18, wherein:
at least one of the one or more tasks includes a planning stage which precedes a corresponding one of the one or more associated voluntary muscle movements.

29. The method of claim 18, wherein improvement in the patient's hemiparesis is assessed according to one or more of the following:
  regarding results of visual inspections (visual inspection results) of the patient's hemiparesis, comparing visual inspection results made before the treatment and made after at least some portion of the treatment had begun;

regarding answers by the patient to a corresponding questionnaire, comparing answers made before the treatment and made after at least some portion of the treatment had begun;

regarding noninvasive mapping of motor cortex representations of a given one of the one or more tasks, comparing mappings made before the treatment and made after at least some portion of the treatment had begun;

regarding objective ratings of the patient's performance of a given one of the one or more tasks, comparing objective ratings made before the treatment and made after at least some portion of the treatment had begun; or regarding subjective ratings of the patient's performance of a given one of the one or more tasks, comparing subjective ratings made before the treatment and made after at least some portion of the treatment had begun.

30. The method of claim 18, wherein:
current comprising the electrical stimulation of the patient's vagus nerve has an amplitude of no less than about 0.8 milliamperes.

31. The method of claim 18, wherein:
the stimulation is electrical stimulation.

32. The method of claim 18, wherein:
the hemiparesis is improved by improving a motor function of the patient.

33. The method of claim 18, wherein:
the hemiparesis is improved by lessening a motor deficit of the patient.

34. The method of claim 18, wherein:
a timing of the stimulation is based on a successful aspect of one or more voluntary muscle movements by the patient.

35. A motor-deficit-therapeutic method for treatment of a patient who has hemiparesis, the method comprising:
for each of one or more tasks that are intended to be performed, instructing a patient to perform at least one repetition of the corresponding task, the corresponding task including one or more associated voluntary muscle movements, and the corresponding task being rehabilitative for hemiparesis; and
during at least partial overlap of at least one of the one or more tasks,
stimulating a vagus nerve of the patient using electrical, magnetic, optical, acoustic or mechanical stimulation which creates an opportunity of motor cortex plasticity in a brain of the patient for a corresponding opportunity period; and
wherein the at least partial overlap pairs the at least one of the one or more tasks and the opportunity-period thereby improving the patient's hemiparesis.

36. The method of claim 35, wherein:
the stimulating of the nerve resulting in raised levels of corresponding neuromodulators in motor cortex of the patient, the raised levels of the corresponding neuromodulators improving the opportunity of motor plasticity thereby improving the patient's hemiparesis.

37. The method of claim 36, wherein:
the neuromodulators include acetylcholine and norepinephrine.

38. The method of claim 35, wherein:
the nerve is a driver of an ascending neuromodulatory system.

39. The method of claim 35, wherein:
the stimulating of the nerve does not directly stimulate motor cortex neurons.

40. The method of claim 35, wherein, for at least one of the one or more tasks, performance by the patient of the one or more associated voluntary muscle movements includes one or more of:
moving one or more extremities of the patient based on a current task to be performed;
reaching at least one hand of the patient towards a targeted object;
touching a targeted object;
grasping the targeted object with at least one hand of the patient; or
moving the targeted object while the targeted object is being grasped with at least one hand of the patient.

41. The method of claim 35, wherein:
performance at least one once of each of the one or more tasks comprises a session; and
two or more sessions comprise a treatment plan (TP).

42. The method of claim 41, wherein:
during the session, at least one of the one or more tasks undergoes one or more repetitions;
at least one task includes one or more associated voluntary muscle movements; and
a timing of the stimulation is based on completion of one of the one or more repetitions.

43. The method of claim 41, wherein:
each session includes about 3 to about 5 tasks;
in each session, each of the tasks undergoes about 30 to about 75 repetitions; and
a duration of each session is in a range of about 30 minutes to about 120 minutes.

44. The method of claim 35, wherein:
for at least one of the one or more tasks, there are substantially no task-associated voluntary muscle movements during an interval between a given one of the one or more associated voluntary muscle movements that comprise the corresponding task and a subsequent one of the one or more associated voluntary muscle movements that comprise the corresponding task, the interval having a duration, T, which is greater than zero, T>0.

45. The method of claim 35, wherein:
at least one of the one or more tasks includes a planning stage which precedes a corresponding one of the one or more associated voluntary muscle movements.

46. The method of claim 35, wherein improvement in the patient's hemiparesis is assessed according to one or more of the following:
regarding results of visual inspections (visual inspection results) of the patient's hemiparesis, comparing visual inspection results made before the treatment and made after at least some portion of the treatment had begun;
regarding answers by the patient to a corresponding questionnaire, comparing answers made before the treatment and made after at least some portion of the treatment had begun;
regarding noninvasive mapping of motor cortex representations of a given one of the one or more tasks, comparing mappings made before the treatment and made after at least some portion of the treatment had begun;
regarding objective ratings of the patient's performance of a given one of the one or more tasks, comparing objective ratings made before the treatment and made after at least some portion of the treatment had begun; or regarding subjective ratings of the patient's performance of a given one of the one or more tasks, comparing subjective ratings made before the treatment and made after at least some portion of the treatment had begun.

47. The method of claim 35, wherein:
current comprising the electrical stimulation of the patient's nerve has an amplitude of no less than about 0.8 milliamperes.

48. The method of claim 35, wherein:
the stimulation is electrical stimulation.

49. The method of claim 35, wherein:
the hemiparesis is improved by improving a motor function of the patient.

50. The method of claim 35, wherein:
the hemiparesis is improved by lessening a motor deficit of the patient.

51. The method of claim 35, wherein:
a timing of the stimulation is based on a successful aspect of one or more voluntary muscle movements by the patient.

52. A therapeutic method for treatment of a patient who has hemiparesis but who does not have a movement disorder disease, the method comprising:
for one or more tasks that are intended to be performed, instructing the patient to perform at least one repetition of each task, each task including one or more associated voluntary muscle movements, and each task being rehabilitative for a hemiparesis; and
during at least partial overlap of at least one of the one or more tasks,
stimulating a vagus nerve of the patient using electrical, magnetic, optical, acoustic or mechanical stimulation thereby improving the patient's hemiparesis.

53. The method of claim 52, wherein:
the stimulating of the vagus nerve resulting in raised levels of corresponding neuromodulators in motor cortex of the patient, the raised levels of the corresponding neuromodulators creating an opportunity of enhanced motor-deficit rehabilitation for a corresponding period (opportunity period); and
the at least partial overlap pairs the at least one of the one or more associated voluntary muscle movements and the opportunity period thereby improving the patient's hemiparesis.

54. The method of claim 53, wherein:
the neuromodulators include acetylcholine and norepinephrine.

55. The method of claim 52, wherein:
the vagus nerve is a driver of an ascending neuromodulatory system.

56. The method of claim 52, wherein:
the stimulating of the vagus nerve does not directly stimulate motor cortex neurons.

57. The method of claim 52, wherein, for at least one of the one or more tasks, performance by the patient of the one or more associated voluntary muscle movements includes one or more of:
moving one or more extremities of the patient based on a current task to be performed;
reaching at least one hand of the patient towards a targeted object;
touching a targeted object;
grasping the targeted object with at least one hand of the patient; or
moving the targeted object while the targeted object is being grasped with at least one hand of the patient.

58. The method of claim 52, wherein:
performance at least once of each the one or more tasks comprises a session; and
two or more sessions comprise a treatment plan (TP).

59. The method of claim 55, wherein:
during the session, at least one of the one or more tasks undergoes one or more repetitions;
at least one task includes one or more associated voluntary muscle movements; and
a timing of the stimulation is based on completion of one of the one or more repetitions.

60. The method of claim 58, wherein:
each session includes about 3 to about 5 tasks;
in each session, each of the tasks undergoes about 30 to about 75 repetitions; and
a duration of each session is in a range of about 30 minutes to about 120 minutes.

61. The method of claim 52, wherein:
for at least one of the one or more tasks, there are substantially no task-associated voluntary muscle movements during an interval between a given one of the one or more associated voluntary muscle movements that comprise the corresponding task and a subsequent one of the one or more associated voluntary muscle movements that comprise the corresponding task, the interval having a duration, T, which is greater than zero, T>0.

62. The method of claim 52, wherein:
at least one of the one or more tasks includes a planning stage which precedes a corresponding one of the one or more associated voluntary muscle movements.

63. The method of claim 52, wherein improvement in the patient's hemiparesis is assessed according to one or more of the following:
regarding results of visual inspections (visual inspection results) of the patient's hemiparesis, comparing visual inspection results made before the treatment and made after at least some portion of the treatment had begun;
regarding answers by the patient to a corresponding questionnaire, comparing answers made before the treatment and made after at least some portion of the treatment had begun;
regarding noninvasive mapping of motor cortex representations of given one of the one or more tasks, comparing mappings made before the treatment and made after at least some portion of the treatment had begun;
regarding objective ratings of the patient's performance of a given one of the one or more tasks, comparing objective ratings made before the treatment and made after at least some portion of the treatment had begun; or
regarding subjective ratings of the patient's performance of a given one of the one or more tasks, comparing subjective ratings made before the treatment and made after at least some portion of the treatment had begun.

64. The method of claim 52, wherein:
current comprising the electrical stimulation of the patient's vagus nerve has an amplitude of no less than about 0.8 milliamperes.

65. The method of claim 52, wherein:
the stimulation is electrical stimulation.

66. The method of claim 52, wherein:
the hemiparesis is improved by improving a motor function of the patient.

67. The method of claim 52, wherein:
the hemiparesis is improved by lessening a motor deficit of the patient.

68. The method of claim 52, wherein:
a timing of the stimulation is based on a successful aspect of one or more voluntary muscle movements by the patient.

* * * * *